United States Patent
Arai et al.

(10) Patent No.: US 8,817,944 B2
(45) Date of Patent: Aug. 26, 2014

(54) X-RAY IMAGING APPARATUS

(75) Inventors: Yoshinori Arai, Chiyoda-ku (JP);
Masakazu Suzuki, Kyoto (JP);
Takahiro Yoshimura, Kyoto (JP);
Makoto Honjo, Kyoto (JP)

(73) Assignees: Nihon University, Tokyo (JP); J. Morita Manufacturing Corporation, Kyoto (JP)

( * ) Notice: Subject to any disclaimer, the term of this patent is extended or adjusted under 35 U.S.C. 154(b) by 330 days.

(21) Appl. No.: 13/207,196

(22) Filed: Aug. 10, 2011

(65) Prior Publication Data
US 2012/0039435 A1 Feb. 16, 2012

(30) Foreign Application Priority Data

Aug. 11, 2010 (JP) ................................. 2010-180619
Jul. 22, 2011 (JP) ................................. 2011-160809

(51) Int. Cl.
| | | |
|---|---|---|
| *A61B 6/03* | (2006.01) | |
| *A61B 6/06* | (2006.01) | |
| *A61B 6/00* | (2006.01) | |
| *A61B 6/14* | (2006.01) | |
| *A61B 19/00* | (2006.01) | |

(52) U.S. Cl.
CPC ... *A61B 6/14* (2013.01); *A61B 6/06* (2013.01);
*A61B 6/035* (2013.01); *A61B 6/03* (2013.01);
*A61B 6/542* (2013.01); *A61B 2019/5259* (2013.01); *A61B 6/4476* (2013.01); *A61B 6/501* (2013.01); *A61B 6/4452* (2013.01); *A61B 6/469* (2013.01)
USPC .................................................. 378/11; 378/4

(58) Field of Classification Search
CPC ........................................................ A61B 6/14
USPC .......................................................... 378/11
See application file for complete search history.

(56) References Cited

U.S. PATENT DOCUMENTS

| | | | |
|---|---|---|---|
| 6,493,415 B1 | 12/2002 | Arai et al. | |
| 2003/0007602 A1* | 1/2003 | Sonobe et al. | 378/108 |
| 2010/0034340 A1 | 2/2010 | Spartiosis et al. | |
| 2010/0067650 A1* | 3/2010 | Arai et al. | 378/16 |
| 2010/0246755 A1* | 9/2010 | Suzuki et al. | 378/11 |

* cited by examiner

FOREIGN PATENT DOCUMENTS

| | | |
|---|---|---|
| EP | 2 210 559 A | 7/2010 |
| JP | 2009-172112 A | 8/2009 |

OTHER PUBLICATIONS

"Two-dimensional interative region-of-interest (ROI) reconstruction . . ." by B. Zhang et al. in Medical Physics of Feb. 13, 2007, vol. 34, No. 3, pp. 935-944.

*Primary Examiner* — Hoon Song
*Assistant Examiner* — Danielle Fox
(74) *Attorney, Agent, or Firm* — DLA Piper LLP (US)

(57) ABSTRACT

In an X-ray imaging apparatus that performs X-ray CT imaging, an X-ray generator (13) that generates an X-ray cone beam (BX1) and an X-ray detector (21) that detects the X-ray cone beam (BX1) radiated to an object (specifically, image object (OB)) are revolved for 180 degrees to be opposed to each other with the object being located therebetween. Further, the X-ray generator (13) is moved such that a revolution reference point (CP) that is set on an optical path (CB) of the X-ray cone beam (BX1) goes round of a predetermined oval shape while the X-ray detector (13) and the X-ray generator (21) are revolved for 180 degrees. Setting is made such that a CT image area (CA) to be imaged by the irradiation of the X-ray cone beam (BX1) has an approximately triangular shape through the above-mentioned operation.

13 Claims, 24 Drawing Sheets

F I G . 2
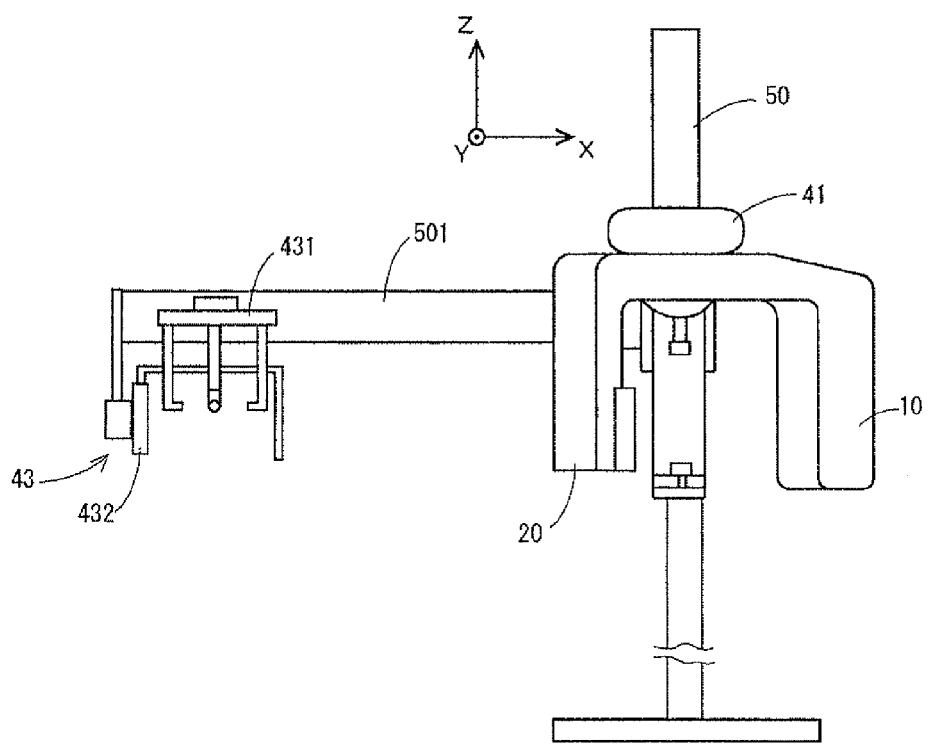

F I G . 8
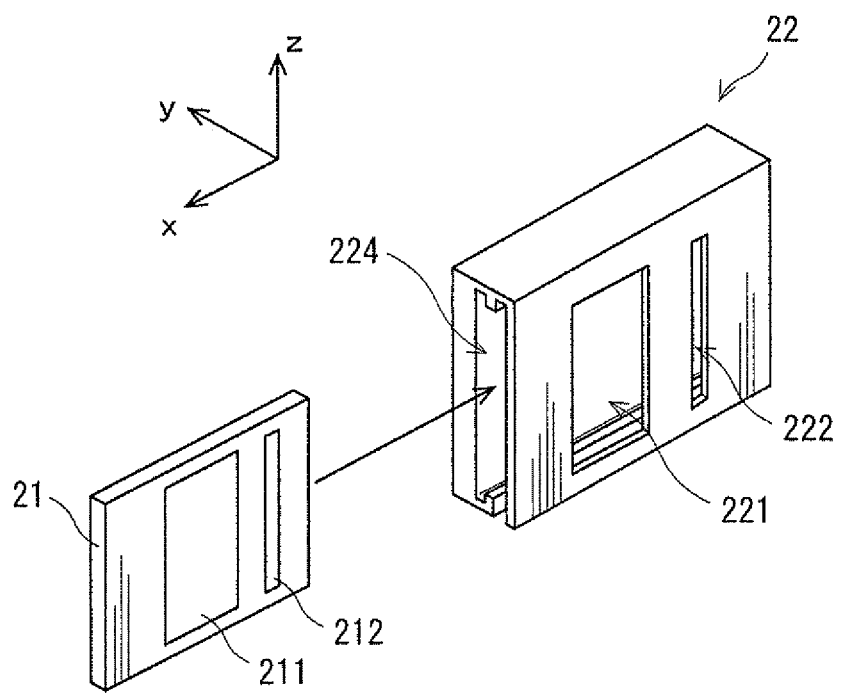

F I G . 1 0
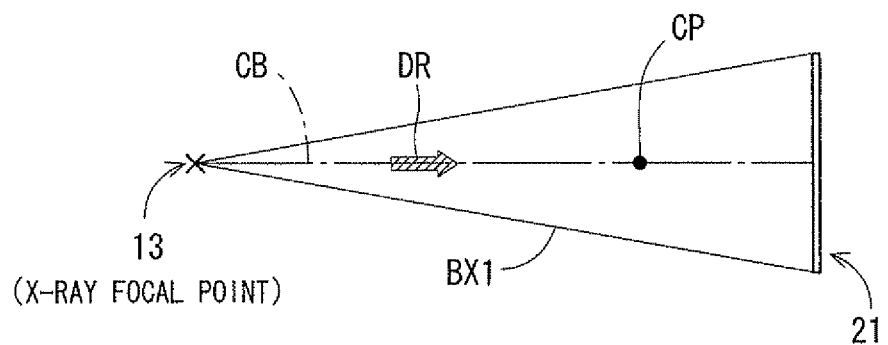

F I G . 1 1
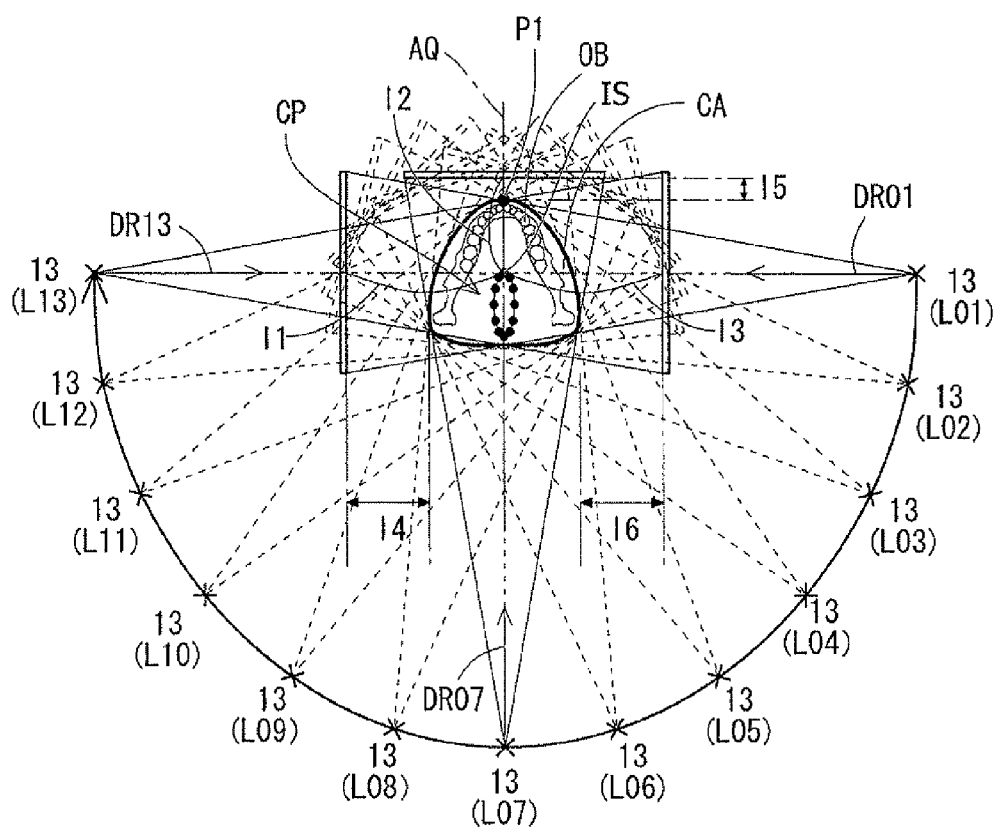

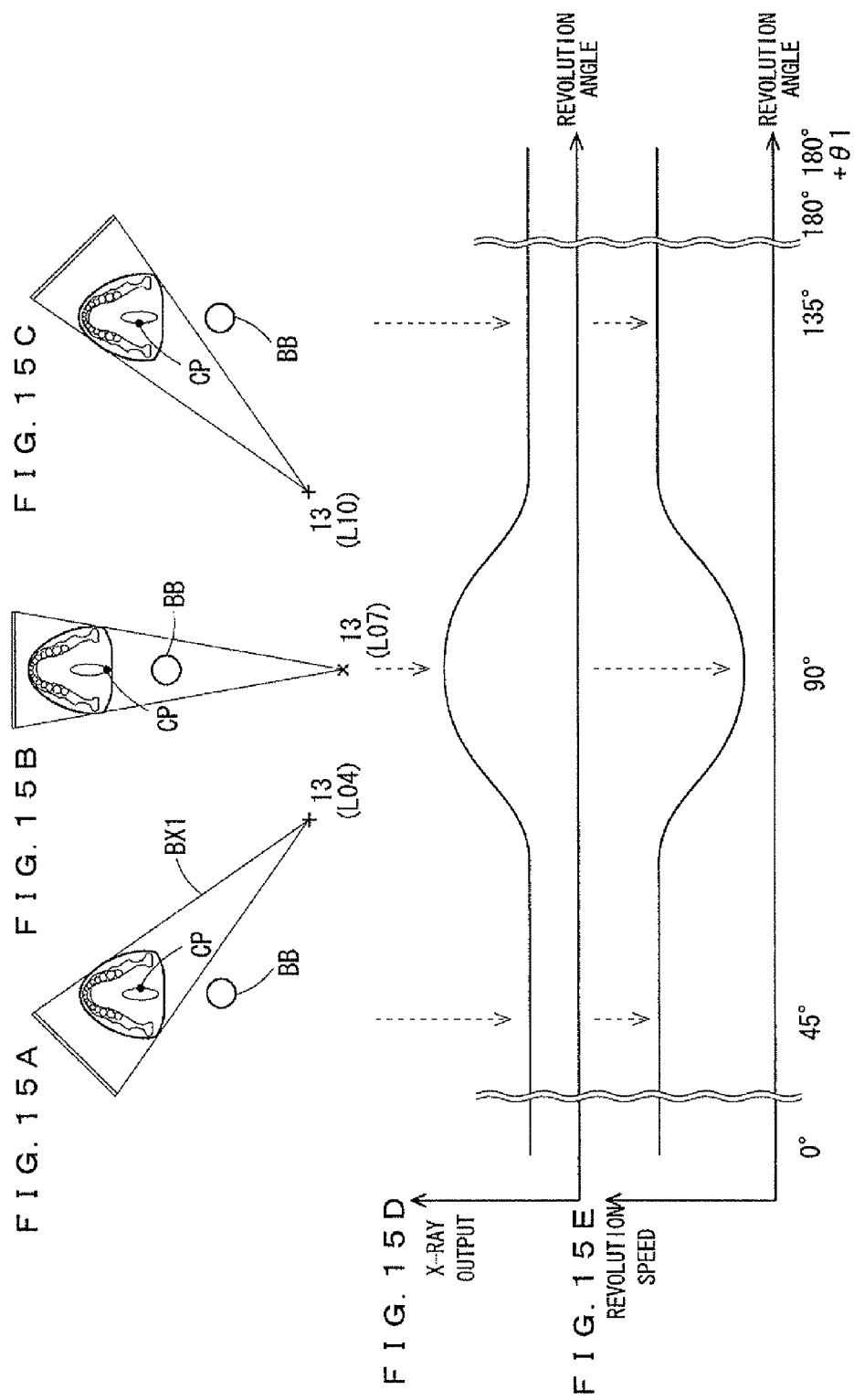

F I G. 1 6
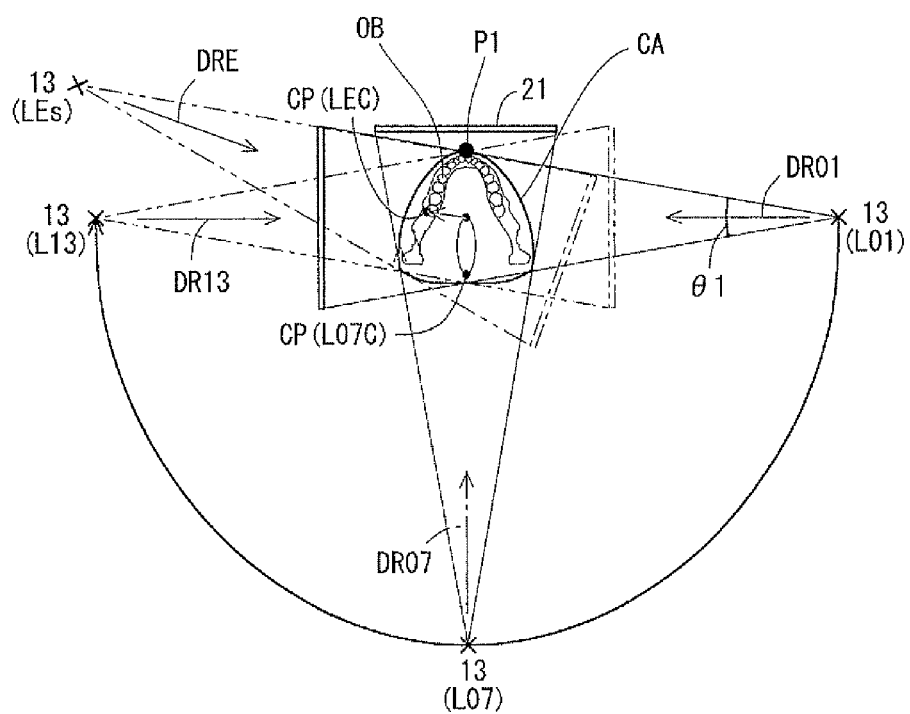

MOVING TRAJECTORY OF REVOLUTION REFERENCE POINT CP

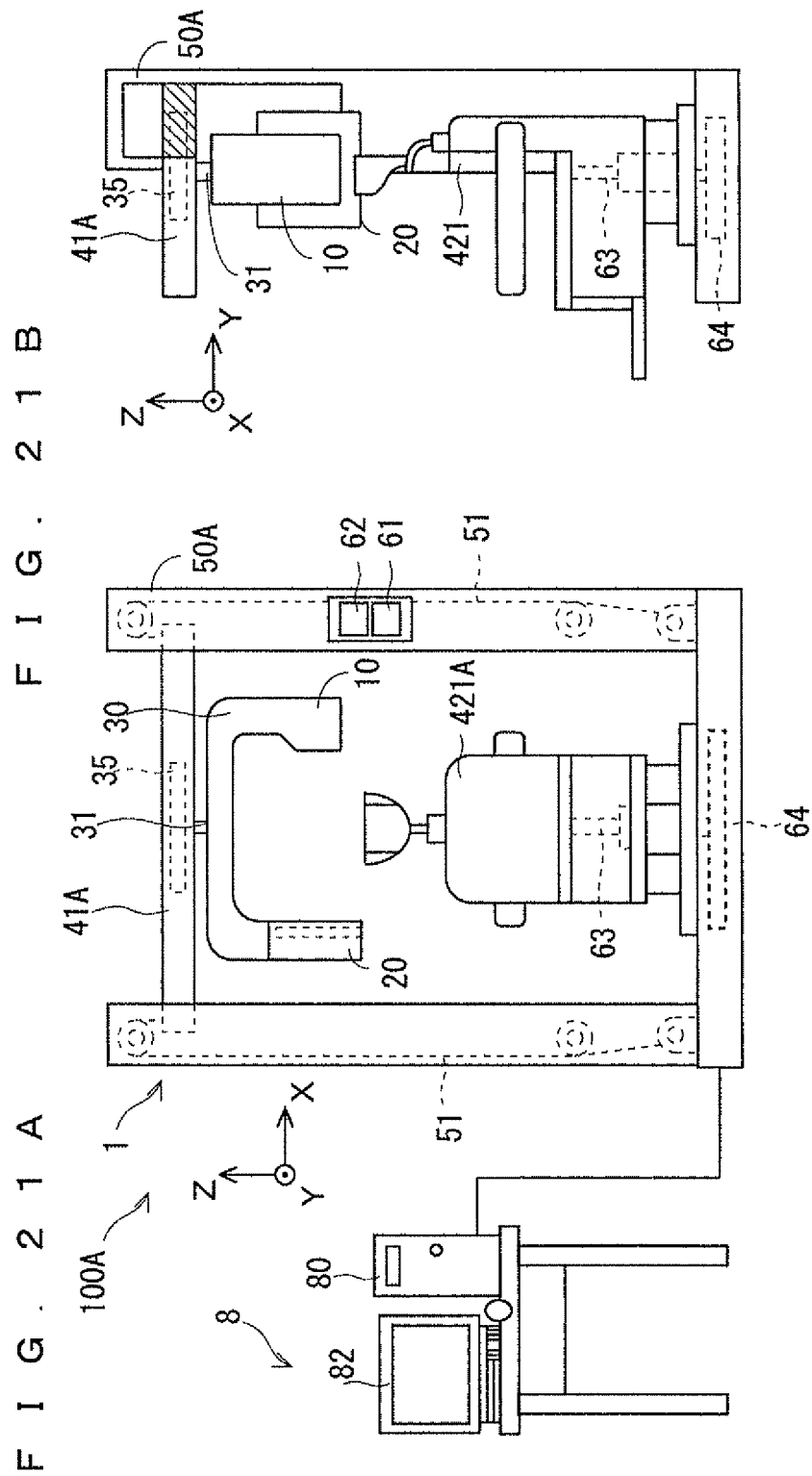

F I G. 2 3 A
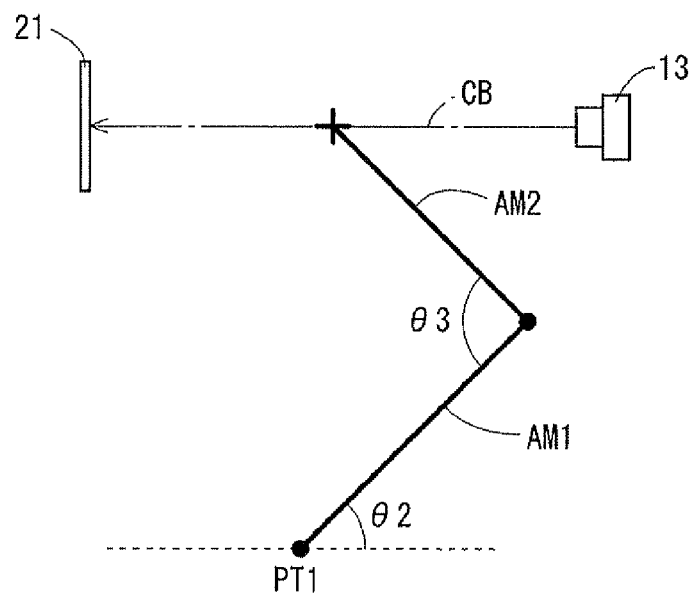
F I G. 2 3 B
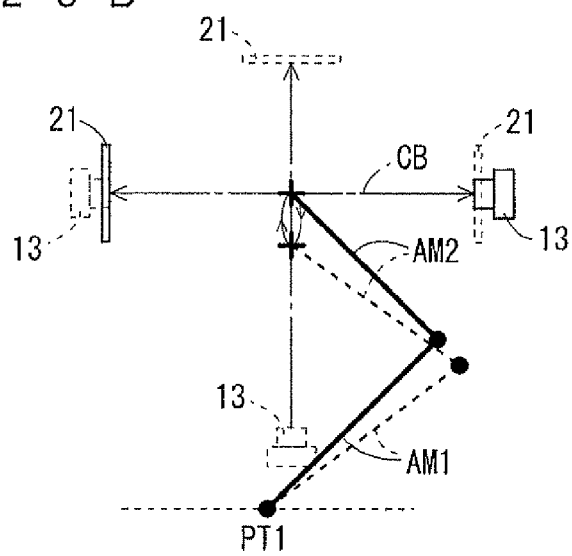

X-RAY IMAGING APPARATUS

BACKGROUND OF THE INVENTION

1. Field of the Invention

The present invention relates to the technology of performing CT imaging with an X-ray.

2. Description of the Background Art

In the medical field or the like, X-ray CT imaging is conventionally performed, in which an X-ray is radiated to an object to collect projection data, and then the obtained projection data is recreated on a computer, to thereby generate computerized tomography images (such as a CT tomographic image and a volume rendering image).

In such X-ray imaging, a cone-shaped X-ray (X-ray cone beam) is radiated to an object from an X-ray generator while the X-ray generator and an X-ray detector are rotated about an object with the object being located between the X-ray generator and the X-ray detector. Then, X-ray detection results (projection data) obtained by the X-ray detector are collected, to thereby recreate three-dimensional data. For example, Japanese Patent No. 3378401 discloses the apparatus that performs X-ray CT imaging as described above.

Japanese Patent No. 3378401 discloses the technology of performing, by an X-ray imaging apparatus, CT imaging of a wider range with a small X-ray detection surface by means of offset scan in which imaging is performed while constantly irradiating a part of an object by displacing the position irradiated with an X-ray cone beam from the center of the object.

In the X-ray imaging apparatus of Japanese Patent No. 3378401, however, a CT image area is circular (also oval), and thus in a case where an area of interest desired to be imaged by an operator is not circular, the areas besides the area of interest are also subjected to X-ray irradiation. This may increase an X-ray exposure amount unnecessarily.

SUMMARY OF THE INVENTION

The present invention is directed to an X-ray imaging apparatus that performs X-ray CT imaging.

According to a first aspect, an X-ray imaging apparatus performing X-ray CT imaging includes: an X-ray generator generating an X-ray cone beam; an X-ray detector detecting the X-ray cone beam radiated to a subject; a support part supporting the X-ray generator and the X-ray detector to be opposed to each other with the subject located therebetween; a revolution driving part revolving the support part relative to the subject; movement mechanisms moving the support part relative to the subject on a two-dimensional plane orthogonal to a revolution shaft of the revolution driving part; and a driving control part controlling the revolution driving part and the movement mechanisms in an interlocking manner such that a CT image area has an approximately triangular shape, the CT image area being imaged by irradiation of the X-ray cone beam while revolving the support part.

According to a second aspect, in the X-ray imaging apparatus according to the first aspect, the driving control part controls, in revolving movements of the X-ray generator and the X-ray detector with the subject being located therebetween, the revolution driving part and the movement mechanisms in an interlocking manner such that a distance between the X-ray detector and any one of right and left ends of a target image area being closer to the X-ray detector when the X-ray detector is located on any one of the right and left of the target image area is larger than a distance between the X-ray detector and the top of the target image area when the X-ray detector is located on a symmetry axis passing through the top of the target image area opposed to a base thereof.

According to a third aspect, in the X-ray imaging apparatus according to the first or second aspect, the approximately triangular shape is obtained by rounding a top portion of an isosceles triangle opposed to a base thereof into a convex arc.

According to a fourth aspect, in the X-ray imaging apparatus according to the third aspect, the approximately triangular shape is obtained by rounding portions at both ends of the base into a convex arc.

According to a fifth aspect, in the X-ray imaging apparatus of the fourth aspect, the approximately triangular shape is a shape obtained by forming center portions of at least two sides other than the base of three sides of the isosceles triangle into a convex arc.

According to a sixth aspect, in the X-ray imaging apparatus of any one of the first, second and fifth aspects, the approximately triangular shape includes extending parts on the right and left of a base thereof and has a symmetrical shape, obtained by connecting the right and left extending parts and the top by a curved line.

According to a seventh aspect, in the X-ray imaging apparatus according to any one of the second, fifth and sixths aspects, the driving control part controls, during X-ray CT imaging, the revolution driving part and the movement mechanisms in an interlocking manner such that a revolution reference point set on an optical axis of the X-ray cone beam generates an oval-shaped moving trajectory while revolving the support part relative to the subject for an amount of a rotation angle of 180 degrees or more and less than 360 degrees.

According to an eighth aspect, in the X-ray imaging apparatus according to the seventh aspect, the revolution driving part is configured to revolve the support part about the revolution shaft relative to the subject secured at a predetermined position, and the revolution shaft serves as the revolution reference point of the X-ray cone beam.

According to a ninth aspect, in the X-ray imaging apparatus according to any one of the first to eighth aspects, the driving control part controls, during CT imaging, the revolution driving part so as to revolve the support part in a relative manner for an amount of a rotation angle obtained by adding an angle of broadening of the X-ray cone beam to 180 degrees in a revolution direction.

According to a tenth aspect, in the X-ray imaging apparatus according to any one of the first, second and fourth to ninth aspects, the CT image area is set such that front teeth and right and left molars of a dental arch model are entirely fit therein, the dental arch model being data set from a standard arrangement of teeth and having a standard dental arch shape.

According to an eleventh aspect, the X-ray imaging apparatus according to any one of the first to tenth aspects further includes an X-ray irradiation control part temporarily increasing, during the X-ray CT imaging, an X-ray amount radiated to the subject in an irradiation state in which the X-ray cone beam radiated to the subject passes through a cervical spine of a head as the subject and then passes through a jaw thereof.

According to a twelfth aspect, in the X-ray imaging apparatus according to any one of the first to eleventh aspects, selection is made between X-ray CT imaging in which the CT image area has an approximately triangular shape and X-ray CT imaging in which a CT image area has a circular shape upon the X-ray generator and the X-ray detector being revolved about a fixed revolution center in imaging.

According to a thirteenth aspect, in the X-ray imaging apparatus according to any one of the first to twelfth aspects, selection is made between the X-ray CT imaging in which the CT image area has an approximately triangular shape and X-ray CT imaging for a jaw local area in which X-ray CT imaging is performed only for a partial area of a jaw smaller than the CT image area having an approximately triangular shape upon the X-ray generator and the X-ray detector being revolved about the partial area of the jaw serving as a fixed revolution center in imaging.

According to the X-ray imaging apparatus of the first aspect, as a result of the CT image area being narrowed approximately in a triangular shape, whereby it is possible to achieve an effect that a detection range of the X-ray detector can be made small.

According to the X-ray imaging apparatus of the second aspect, it is possible to achieve an effect that a CT image area having an approximately triangular shape can be easily formed.

According to the X-ray imaging apparatus of the third aspect, it is possible to achieve an effect that the X-ray exposure amount of the subject can be reduced further in a case where the CT image area is an area of interest that includes an image object having an approximately semi-circular shape (including an approximately semi-oval shape).

According to the X-ray imaging apparatus of the fourth aspect, it is possible to achieve an effect that the X-ray exposure amount of the subject can be reduced more compared with the third aspect in a case where the CT image area is an area of interest that includes an image object having an approximately semi-circular shape (including an approximately semi-oval shape).

According to the X-ray imaging apparatus of the fifth and sixth aspects, in particular, it is possible to achieve an effect that a CT image area, which is more suitable for the shape of an image target compared with the fourth aspect, can be set in a case where the CT image area is an area of interest including an image target having an approximately semi-circular shape (including an approximately semi-oval shape).

According to the X-ray imaging apparatus according to the seventh aspect, it is possible to perform X-ray CT imaging with the range narrowed further from a circular shape or an oval shape being the CT image area. This reduces the X-ray exposure amount of the subject in X-ray CT imaging. In addition, it is possible to narrow the irradiation range of the X-ray cone beam, and thus the detection range of the X-ray detector can be narrowed as well, which reduces a manufacturing cost.

According to the X-ray imaging apparatus of the eighth aspect, the revolution shaft serves as the revolution reference point of the X-ray cone beam, which facilitates control. Accordingly, it is possible to achieve an effect that the CT image area having an approximately triangular shape can be easily formed.

According to the X-ray imaging apparatus of the ninth aspect, it is possible to irradiate all points within the CT image area with the X-rays from respective directions in the range of 180 degrees. This achieves an effect that a highly accurate CT image can be obtained in the CT image area.

According to the X-ray imaging apparatus of the tenth aspect, the CT image area is set so as to include a dental arch model, whereby it is possible to achieve an effect that an area including upper and lower teeth are entirely included in actuality can be imaged well.

According to the X-ray imaging apparatus of the eleventh aspect, X-ray CT imaging can be performed in consideration of the X-ray amount absorbed by the cervical spine, whereby it is possible to achieve an effect that a sufficient dose of X-ray cone beams can be radiated to the area including the upper and lower teeth.

Therefore, an object of the present invention is to provide the technology capable of achieving miniaturization of an X-ray detection surface while reducing an X-ray exposure amount of a subject.

These and other objects, features, aspects and advantages of the present invention will become more apparent from the following detailed description of the present invention when taken in conjunction with the accompanying drawings.

BRIEF DESCRIPTION OF THE DRAWINGS

FIG. 2 is a front view showing a cephalostat applicable to the X-ray imaging apparatus;

FIG. 8 is a perspective view showing a detector holder;

FIG. 10 is a plan view conceptually showing an X-ray cone beam;

FIG. 11 is a plan view conceptually showing the state of imaging an image of an image object;

FIGS. 15A, 15B, 15C, 15D and 15E are figures for describing the state in which an X-ray amount radiated to an object is adjusted during the CT imaging shown in FIG. 14A;

FIG. 16 is a plan view showing an outline of other CT imaging;

FIGS. 21A and 21B show an outline of an X-ray imaging apparatus according to a second embodiment;

FIGS. 23A and 23B are views for describing a movement mechanism according to a modification.

DESCRIPTION OF THE EMBODIMENTS

Hereinafter, embodiments are described in detail with reference to the accompanying drawings. Any components described in these embodiments are merely illustrative, and should not be construed as limiting the scope of the present invention.

1. First Embodiment

1.1. Configuration and Function of X-Ray Imaging Apparatus

Figure 1:
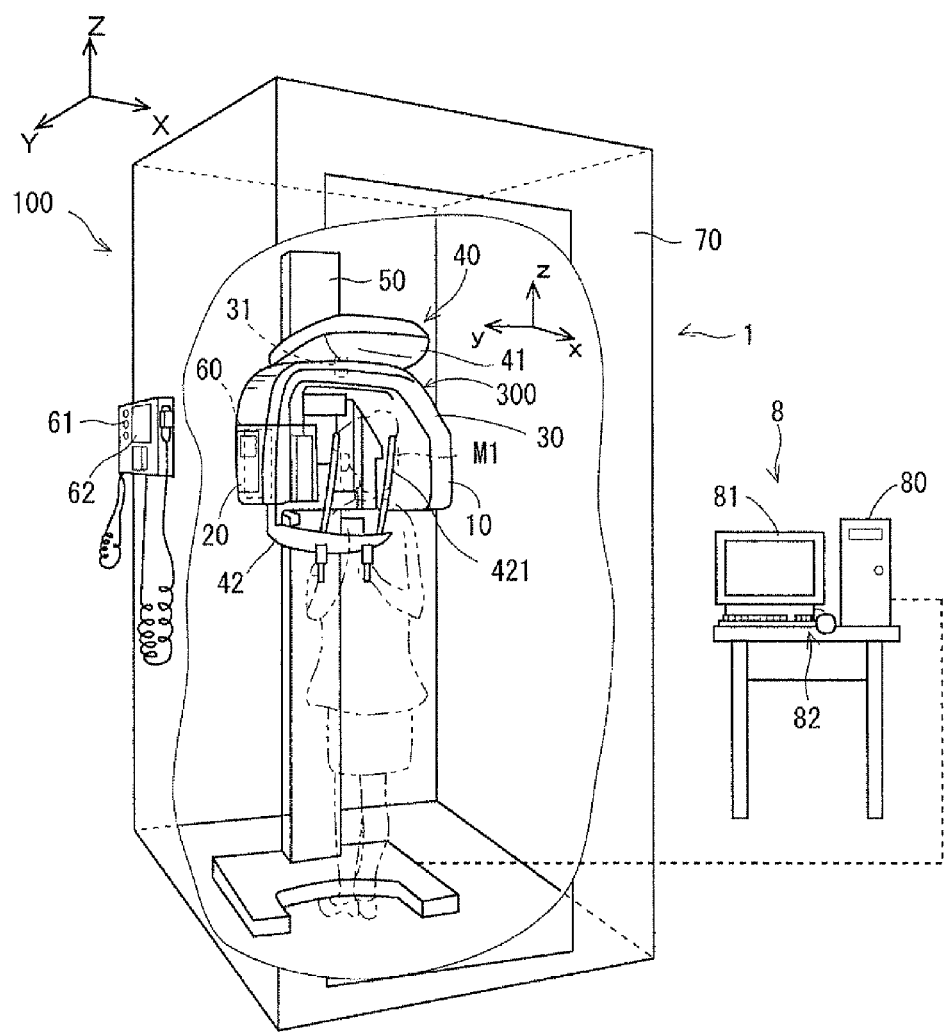
FIG. 1 is a schematic perspective view showing an X-ray imaging apparatus according to a first embodiment.

FIG. 1 is a schematic perspective view showing an X-ray imaging apparatus 100 according to a first embodiment. The X-ray imaging apparatus 100 is roughly divided into a main body unit 1 that executes X-ray CT imaging to collect projection data and an information processing device 8 that processes the projection data collected by the main body unit 1 to generate various images.

The main body unit 1 includes an X-ray generation part 10, an X-ray detection part 20, a support part 300 (a support means, revolution arm 30), an elevator part 40, a support column 50 and a main-body control part 60. The X-ray generation part 10 emits an X-ray cone beam BX1 having an X-ray flux toward an object M1. The X-ray detection part 20 detects the X-ray emitted by the X-ray generation part 10. The support part 300 supports each of the X-ray generation part 10 and the X-ray detection part 20. The elevator part 40 holds the support part 300 (revolution arm 30) in a suspending manner and is capable of moving up and down in the vertical direction with respect to the support column 50. The support column 50 extends in the vertical direction. The X-ray cone beam BX1 is formed into a pyramid shape or a cone shape by an X-ray restriction part, as described below.

The X-ray generation part 10 and the X-ray detection part 20 are respectively fixed to both ends of the revolution arm 30 in a suspended manner, which are supported so as to be opposed to each other with the object M1 therebetween while X-ray imaging. The revolution arm 30 is fixed to the elevator part 40 in a suspended manner through a revolution shaft 31 extending in the vertical direction.

While the support part 300 is configured as the revolution arm 30 that revolves about the revolution shaft 31 and the X-ray generation part 10 and the X-ray detection part 20 are respectively mounted to both ends of the revolution arm 30 having an approximately rectangular solid shape in the present embodiment, the configuration of the support part 300 that supports the X-ray generation part 10 and the X-ray detection part 20 is not limited thereto. The X-ray generation part 10 and the X-ray detection part 20 may be supported by, for example, a member that rotates about the center of an annular-shaped portion so as to be opposed to each other.

In the following description, the direction (herein, vertical direction) parallel to an axial direction of the revolution shaft 31 is referred to as a "Z-axis direction", a direction intersecting the Z-axis direction is referred to as an "X-axis direction", and a direction intersecting the X-axis direction and the Z-axis direction is referred to as a "Y-axis direction". The X-axis and the Y-axis directions can be set appropriately. Herein, the right-and-left direction of a subject, which is the object M1, when the subject is positioned in the X-ray imaging apparatus 100 to face the support column 50 is defined as the X-axis direction, whereas the front-and-back direction of the subject is defined as the Y-axis direction. The X-axis direction, the Y-axis direction and the Z-axis direction are assumed to be perpendicular to each other in the present embodiment. In some cases, the Z-axis direction is referred to as the vertical direction, and the direction on the plane two-dimensionally defined by the X-axis direction and the Y-axis direction is referred to as the horizontal direction.

As to the three-dimensional coordinates on the revolution arm 30, on the other hand, the direction in which the X-ray generation part 10 and the X-ray detection part 20 are opposed to each other is referred to as a "y-axis direction", a horizontal direction perpendicular to the y-axis direction is referred to as an "x-axis direction", and a vertical direction perpendicular to the x-axis and y-axis directions is referred to as a "z-axis direction". In the present embodiment and the following embodiments, the Z-axis direction is the same as the z-axis direction. The revolution arm 30 in the present embodiment rotates about the revolution shaft 31 extending in the vertical direction. Accordingly, the xyz perpendicular coordinate system rotates about the Z-axis (=z-axis) with respect to the XYZ perpendicular coordinate system.

As shown in FIG. 1, when the X-ray generation part 10 and the X ray detection part 20 are viewed from above in plan view, the direction from the X-ray generation part 10 toward the X-ray detection part 20 is referred to as a (+y) direction, the horizontal direction perpendicular to the (+y) direction, which extends rightward in FIG. 1 (in the direction of the revolution arm 30 shown in FIG. 1, direction toward the front of the object M1 shown in FIG. 1), is referred to as a (+x) direction, and a vertically upward direction is referred to as a (+z) direction.

The elevator part 40 is engaged with the support column 50 vertically arranged so as to extend along the vertical direction. An upper fame 41 and a lower frame 42 of the elevator part 40 protrude toward the side opposite to the side on which the elevator part 40 is engaged with the support column 50, and thus the elevator part 40 has an approximately U-shaped structure.

An upper end portion of the revolution arm 30 is mounted to the upper frame 41. The revolution arm 30 is suspended from the upper frame 41 of the elevator part 40 in this manner, and the revolution arm 30 is moved up and down as a result of the elevator part 40 moving along the support column 50.

The lower frame 42 is provided with an object fixing part 421 including an ear rod for fixing the object M1 (human head in this case) from the right and left sides and a chin rest for fixing a chin. The revolution arm 30 is moved up and down in accordance with the height of the object M1 as well as in accordance with moving up and down of the elevator part 40 so as to be adjusted to an appropriate position, with the result that the object M1 is fixed by the object fixing part 421. The object fixing part 421 fixes the object M1 such that the body axis of the object M1 is identical to or substantially identical to the axis direction of the revolution shaft 31.

As shown in FIG. 1, the main-body control part 60 that controls the operations of the respective components of the main-body unit 1 is provided in the X-ray detection part 20. Further, the respective components of the main body unit 1 are accommodated in an X-ray proof room 70. A display part 61 and an operation panel 62 are provided to the outside wall of the X-ray proof room 70. The display part 61 is configured as a liquid crystal monitor for displaying various information based on the control of the main-body control part 60 and the like. The operation panel 62 is configured as buttons for input of various instructions for the main-body control part 60 and the like. The operation panel 62 is also used for designating, for example, the position of an image area of a living organ or the like. There are various modes in X-ray imaging, which can be selected by an operation of the operation panel 62.

The information processing device 8 includes an information processing main body 80 configured as a computer, a work station or the like, and is capable of sending/receiving various data with the main body unit 1 by means of a communication cable. Note that data may be exchanged between the main body unit 1 and the information processing device 8 in a wireless manner.

The information processing device 8 processes the projection data obtained by the main body unit 1 to recreate three-dimensional data (volume data) expressed by voxels. For example, the information processing device 8 is capable of setting a specific plane in the three-dimensional data to recreate a tomographic image of the specific plane.

A display part 81 including a display device such as a liquid crystal monitor and an operation part 82 composed of a keyboard, a mouse and the like are connected to the information processing main body 80. An operator is capable of providing various commands to the information processing device 8 by means of the operation part 82. It is also possible to configure the display part 81 as a touch panel and, in this case, the display part 81 serves a part or the whole of the functions of the operation part 82.

FIG. 2 is a front view showing a cephalostat 43 applicable to the X-ray imaging apparatus 100. As shown in FIG. 2, the cephalostat 43 may be provided to the elevator part 40. For example, the cephalostat 43 is mounted to an arm 501 extending from the middle of the support column 50 in the horizontal direction. The cephalostat 43 may be provided with a fixture 431 for fixing a head at a fixed position and an X-ray detector 432 for cephalic imaging. Various cephalostats such as one disclosed in Japanese Patent Application Laid-Open No. 2003-245277 are adoptable as the cephalostat 43.

Figure 3:
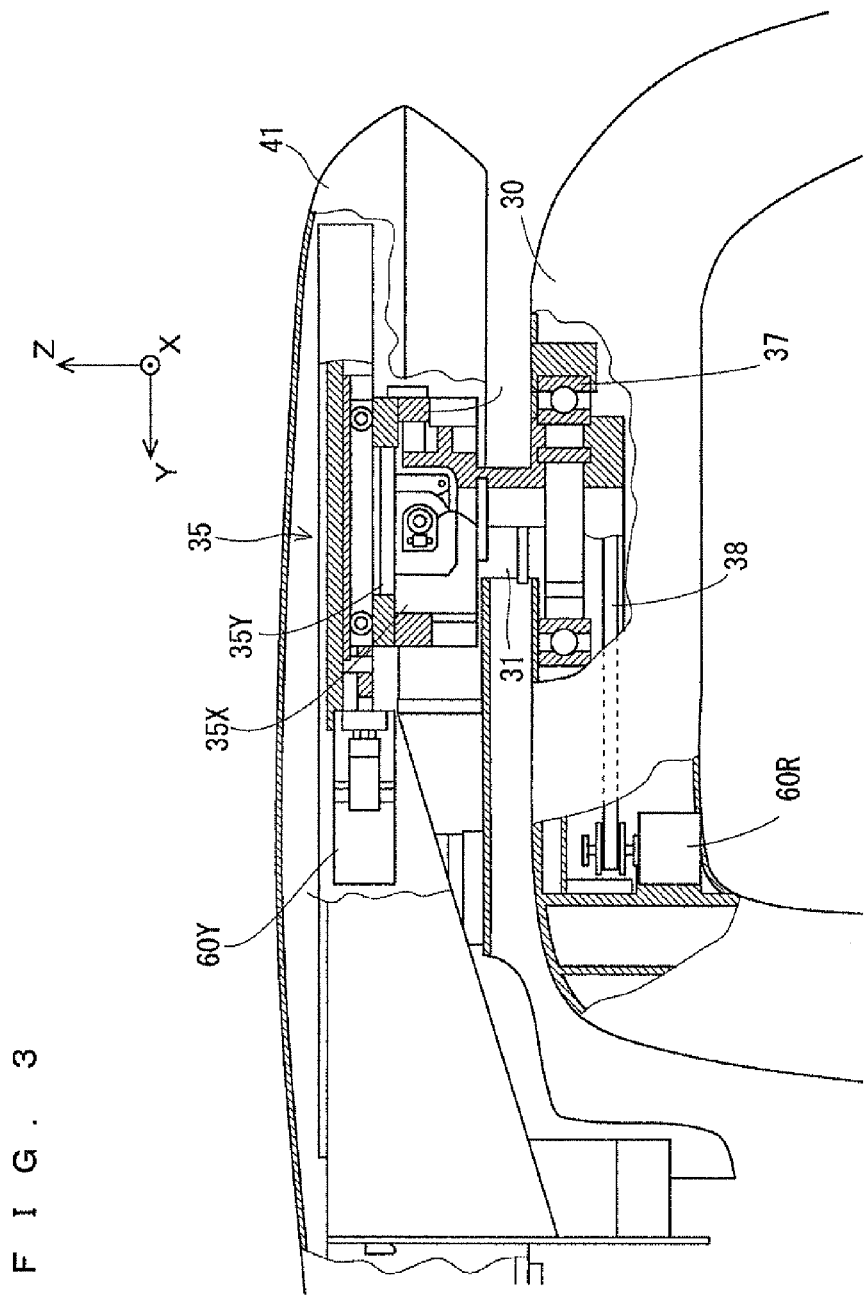
FIG. 3 is a partial cross-sectional view showing a revolution arm and an upper frame together with internal structures thereof.
Figure 4:
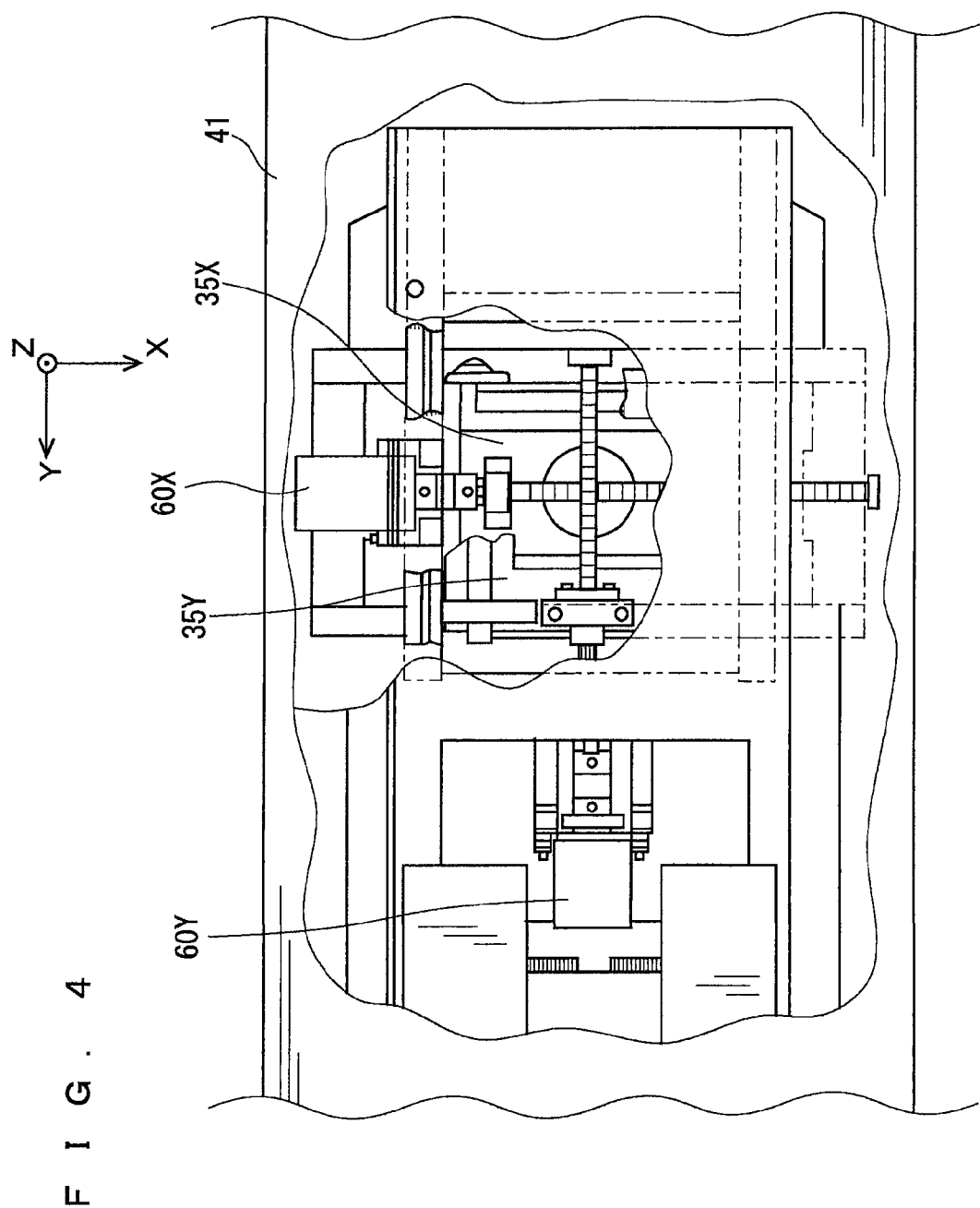
FIG. 4 is a partial cross-sectional view showing the upper frame together with the internal structure thereof.

FIG. 3 is a partial cross-sectional view showing the revolution arm 30 and the upper frame 41 together with the internal structures thereof. FIG. 4 is a partial cross-sectional view showing the upper frame 41 together with the internal structure thereof. FIG. 3 shows the revolution arm 30 and the upper frame 41 when the X-ray imaging apparatus 100 is viewed from the side, and FIG. 4 shows the upper frame 41 when the X-ray imaging apparatus 100 is viewed from above.

The upper frame 41 includes an XY-table 35 composed of a Y-table 35Y and an X-table 35X. The Y-table 35Y moves in the front-and-back direction (Y-axis direction) on the revolution arm 30, and the X-table 35X is supported by the Y-table 35Y and moves in the right-and-left direction (X-axis direction) thereon. In addition, the upper frame 41 includes an Y-axis motor 60Y for driving the Y-table 35Y, an X-axis motor 60X for moving the X-table 35X in the X-axis direction with respect to the Y-table 35Y, and a revolution motor 60R for revolving the revolution arm 30 about the revolution shaft 31 that connects the X-table 35X and the revolution arm 30. While the revolution shaft 31 is configured to extend along the vertical direction in the present embodiment, the revolution shaft may be tilted at an appropriate angle with respect to the vertical direction.

Provided between the revolution shaft 31 and the revolution arm 30 is a bearing 37, which allows the revolution arm 30 to rotate easily with respect to the revolution shaft 31. The revolution motor 60R is fixed inside the revolution arm 30, and transmits rotational force to the revolution shaft 31 by means of a belt 38 to revolve the revolution arm 30.

The revolution shaft 31, the bearing 37, the belt 38 and the revolution motor 60R are merely examples of a revolution mechanism for revolving the revolution arm 30, and the revolution mechanism of the revolution arm 30 is not limited thereto. For example, the revolution mechanism shown in FIG. 3 is configured to revolve the revolution arm 30 with respect to the revolution shaft 31 that does not rotate. In this case, there may be provided a bearing (not shown) between the revolution shaft 31 and the X-table 35X such that the revolution shaft 31 turns with respect to the X-table 35X and that the revolution arm 30 is fixed to the revolution shaft 31. Further, the revolution shaft 31 may be rotated by a motor (not shown) provided to the X-table 35X, to thereby revolve the revolution arm 30.

In the X-ray imaging apparatus 100, control motors such as the X-axis motor 60X, the Y-axis motor 60Y and the revolution motor 60R are driven in accordance with a predetermined program, with the result that the X-table 35X and the Y-table 35Y are moved in the right-and-left direction (X direction) and the back-and-forth direction (Y direction), respectively, while revolving the revolution arm 30. As a result, the movement of the revolution shaft 31 is two-dimensionally controlled rightward and leftward as well as back and forth, in the X-Y directions. The X-axis motor 60X and the Y-axis motor 60Y serve as a movement mechanism (a movement means) in the present embodiment.

{X-Ray Generation Part 10}

Figure 5:
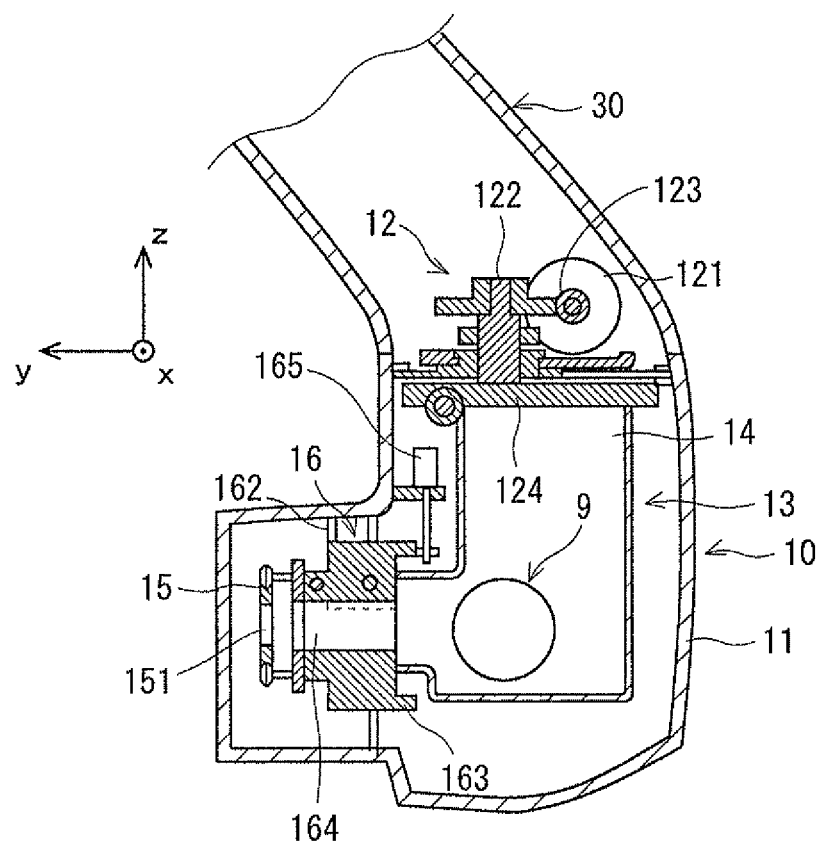
FIG. 5 is a vertical cross-sectional view showing the inside of an X-ray generation part.
Figure 6:
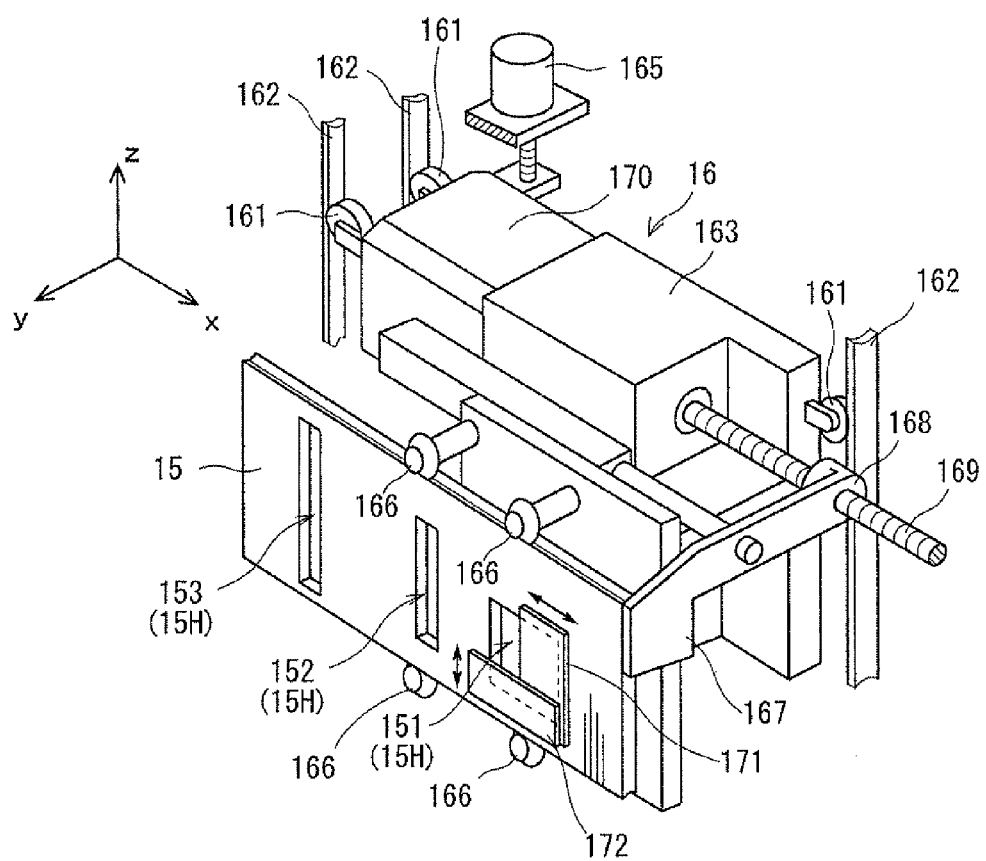
FIG. 6 is a perspective view showing a beam shaping mechanism.

FIG. 5 is a vertical cross-sectional view showing an inside of the X-ray generation part 10. FIG. 6 is a perspective view showing a beam shaping mechanism 16. As shown in FIG. 5, the X-ray generation part 10 includes a housing 11 for accommodating the respective components of the X-ray generation part 10. The housing 11 is coupled with the revolution arm 30 via the rotation mechanism 12.

The housing of the revolution arm 30 and the housing 11 of the X-ray generation part 10 may be integrated with each other so as to obtain the structure in which the X-ray generator 13 is coupled with the revolution arm 30 via the rotation mechanism 12, whereby the rotation mechanism 12 turns the X-ray generator 13 inside the housing 11.

The rotation mechanism 12 includes a rotation motor 121 fixed inside the revolution arm 30, a vertical shaft 122 rotatably fixed to the revolution arm 30, a gear mechanism 123 for coupling the rotation motor 121 with the vertical shaft 122, and a fixed member 124 fixed to the housing 11 and the vertical shaft 122. Driving of the rotation motor 121 is transmitted to the vertical shaft 122 via the gear mechanism 123, whereby the vertical shaft turns.

The housing 11 is configured to be rotatable about the vertical shaft 122 in a horizontal plane by driving of the rotation motor 121 that operates based on a control signal from the main-body control part 60 described below. The above-mentioned rotation mechanism 12 is used in, for example, cephalic imaging.

The configuration is not necessarily made such that an X-ray beam is radiated while the rotation motor 121 turns the housing 11. For example, the housing 11 may be caused to stop turning after the X-ray generation part 10 points in the specified direction, and the object M1 may be scanned with an X-ray beam while moving a beam shaping plate 15 on the front surface of the X-ray generator 13, which is described below, to move a beam passing hole 152. That is, the structure as disclosed in Japanese Patent Application Laid-Open No. 2003-245277 filed by the applicant of the present application may be adopted.

Further, cephalic imaging may be performed while revolving the revolution arm 30 by driving of the revolution motor 60R, not by driving of the rotation motor 121.

The X-ray generator 13 is accommodated in the housing 11. The X-ray generator 13 is formed of an X-ray tube 9 that is an X-ray source and an X-ray shield casing 14 that covers the X-ray tube 9 except for a portion thereof (left side in FIG. 5) opposed to the X-ray detection part 20. In the X-ray shield casing 14, the beam shaping plate 15 is provided in a region opposed to the X-ray detection part 20. The beam shaping plate 15 is attached to the beam shaping mechanism 16.

As shown in FIG. 6, the beam shaping mechanism 16 includes a block 163 supported so as to move up and down along a plurality of vertical guide rails 162 with a plurality of guide rollers 161 provided therebetween. The block 163 has an X-ray passing hole 164 (see FIG. 5) for guiding the X-ray emitted from the X-ray tube 9 toward the X-ray detection part 20.

The block 163 is coupled with an elevation motor 165 fixed to the housing 11, through a screw mechanism. Driving of the elevation motor 165 allows the X-ray generation part 10 to move an X-ray radiation angle in the Z-axis direction. As a result, the X-ray radiation angle can be moved up and down without moving the X-ray generation part 10 up and down.

The beam shaping plate 15, which shapes the X-ray beam emitted from the X-ray tube 9 and has a plurality of openings for passing a plurality of X-rays therethrough, is provided on the front side (outside of the X-ray passing hole 164) of the block 163. The beam shaping plate 15 serves as the X-ray restriction part that partially shields passing of the X-ray and restricts the radiation range. The beam shaping plate 15 is supported so as to move horizontally by a plurality of guide rollers 166 fixed to the front surface of the block 163.

Coupled with one end of the beam shaping plate 15 is a coupling arm 167. A nut 168 is attached to the coupling arm 167. The block 163 rotatably supports a screw shaft 169 extending in the longitudinal direction of the beam shaping plate 15. The nut 168 is screwed with the screw shaft 169, and the screw shaft 169 is coupled with a motor 170 fixed to the block 163.

The beam shaping plate 15 is moved exclusively, in the front portion of the block 163, to horizontal direction, that is, in the direction intersecting the X-ray beam, by driving of the motor 170 that operates based on the control signal from the main-body control part 60.

In the present embodiment, the beam shaping plate 15 has three types of X-ray passing openings (primary slit, collimator). The three types of X-ray passing openings include a beam passing hole 151 for CT imaging, a beam passing hole 153 for panoramic imaging and a beam passing hole 152 for cephalic imaging. The beam passing hole 151 is rectangular or square in shape for shaping an X-ray beam into an X-ray cone beam having a cone shape (also including a pyramid shape), the beam passing hole 153 is vertically long for shaping an X-ray beam into an elongated belt shape to obtain a narrow beam, and the beam passing hole 152 is also vertically long.

For example, in a case where the beam passing hole 151 for X-ray CT imaging is opposed to the X-ray tube 9, the X-ray generation part 10 emits an X-ray cone beam spreading in a truncated pyramid shape, toward the X-ray detection part 20. Assuming that the beam passing hole 151 for X-ray CT imaging has the same size vertically and horizontally, the X-ray cone beam has an approximately square cross section perpendicular to the traveling direction of the X-ray. The beam passing hole 151 may be formed in a circular shape such that a conic-shaped X-ray cone beam is radiated.

In a case where the beam passing hole 153 for panoramic imaging or the beam passing hole 152 for cephalic imaging is opposed to the X-ray tube 9, the X-ray generation part 10 emits an X-ray cone beam that has an approximately flat-plate shape and has a vertically long cross section (more strictly, truncated-pyramid shape), toward the X-ray detection part 20.

Provided on the front surface of the beam shaping plate 15 is a blocking plate 171 that is moved in the horizontal direction to partially block the opening of the beam passing hole 151. The blocking plate 171 is connected to a horizontal movement mechanism configured as an actuator (not shown) and is configured to be movable in the horizontal direction with respect to the beam shaping plate 15. Provided in front of the blocking plate 171 on the front surface of the beam shaping plate 15 is a blocking plate 172 that is moved in the vertical direction to partially block the opening of the beam passing hole 151. The blocking plate 172 is connected to a vertical movement mechanism configured as an actuator (not shown) and is configured to be movable in the vertical direction with respect to the beam shaping plate 15. The beam shaping mechanism 16 moves the blocking plate 171 in the horizontal direction based on the control signal from the main-body control part 60, to thereby partially block the X-ray passing through the beam passing hole 151. This restricts the spread (width) of the X-ray cone beam in the horizontal direction. The function of restricting passing of the X-ray is used when a mode for imaging of a relatively small range is performed in X-ray CT imaging. As described above, the beam shaping mechanism 16 forms the restriction part for restricting passing of the X-ray in the present embodiment.

An amount of the spread of the X-ray cone bean in the horizontal direction can be adjusted by an amount of movement of the blocking plate 171 with respect to the beam passing hole 151, and the irradiation direction of the X-ray cone beam in the horizontal direction can be adjusted by an amount of driving of the beam shaping plate 15 by the motor 170.

The beam shaping mechanism 16 moves the blocking plate 172 in the vertical direction based on the control signal of the main-body control part 60, to thereby partially block the X-ray passing through the beam passing hole 151. This restricts the spread (width) of the X-ray cone beam in the vertical direction. The function of restricting passing of the X-ray is used when a mode for imaging only the maxilla range or only the mandible range is performed in X-ray CT imaging.

In the state in which the blocking plate 172 is retracted so as not to block the beam passing hole 151, X-ray CT imaging is performed in the mode in which the maxilla and mandible are both irradiated with the X-ray cone beam.

An amount of the spread of the X-ray cone beam in the vertical direction can be adjusted by an amount of movement of the blocking plate 172 with respect to the beam passing hole 151. The irradiation direction of the X-ray cone beam in the vertical direction can be adjusted by an amount of driving of the block 163 by the motor 165, and besides, by the amount of driving of the beam shaping plate 15.

It is briefly shown in FIG. 6 that only the blocking plate 171 is provided on the front surface of the beam shaping plate 15. However, FIG. 6 is shown for easy understanding of the mechanical configuration of X-ray blocking, and in actuality, the blocking plate 171 is driven by the actuator configured as a motor (not shown) or the like as described above. The configuration of the blocking plate 171 is not limited thereto. That is, any configuration is adoptable as long as the spread (width) of the X-ray cone beam in the horizontal direction can be restricted. Therefore, a blocking member (not shown) configured to be movable so as to partially block the X-ray cone beam in front of the beam passing hole 151 may be provided independently of the beam shaping plate 15.

Specifically, a conceivable example of the structure of the above-mentioned blocking member is the structure in which, for example, a blocking member is guided by a guide member in the horizontal direction (between right side and left side), and the blocking member is driven in the horizontal direction by turning, by a motor, a screw shaft screwed with the screw hole provided in the blocking member.

The blocking member and its drive mechanism may be composed of a plurality of sets thereof. For example, two blocking members that move independently may block one end and the other end (left end and right end) of the X-ray cone beam in the horizontal direction by an appropriate amount of blocking, so that the X-ray cone beam is radiated to an appropriate location with an appropriate width as to the spread (width) of the X-ray cone beam in the horizontal direction.

Similarly to the blocking member 171, it is briefly shown in FIG. 6 that only the blocking plate 172 is provided on the front surface of the beam shaping plate 15. However, FIG. 6 is shown for easy understanding of the mechanical configuration of X-ray blocking, and in actuality, the blocking plate 172 is driven by the actuator configured as a motor (not shown) or the like as described above. The configuration of the blocking plate 172 is not limited thereto. That is, any configuration is adoptable as long as the spread (width) of the X-ray cone beam in the vertical direction can be restricted. Therefore, a blocking member (not shown) configured to be movable so as to partially block the X-ray cone beam in front of the beam passing hole 151 may be provided independently of the beam shaping plate 15.

Specifically, a conceivable example of the structure of the above-mentioned blocking member is the structure in which, for example, a blocking member having a screw V hole is guided by a guide member in the vertical direction (between upper side and lower side), and the blocking member is driven in the vertical direction by, by a motor, turning a screw shaft screwed with the screw hole provided in the blocking member.

The blocking member and its drive mechanism may be composed of a plurality of sets thereof. For example, two blocking members that move independently may block one end and the other end (upper end and lower end) of the X-ray cone beam in the vertical direction by an appropriate amount of blocking, so that the X-ray cone beam is radiated to an appropriate location with an appropriate width as to the spread (width) of the X-ray cone beam in the vertical direction.

In the description below, the above-mentioned mechanisms that restrict the spread of the X-ray cone beam in the horizontal direction and the vertical direction are also referred to as a horizontal beam shaping mechanism and a vertical beam shaping mechanism, respectively.

The width of the X-ray passing hole 164 of the block 163 in the horizontal direction may be the same as the width of the beam passing hole 151 in the horizontal direction so as to adjust the degree of opening of the cone beam in the horizontal direction by the movement of the beam shaping plate 15 by driving of the motor 170.

In this case, it suffices that, for irradiation with the maximum width of spreading of the X-ray cone beam in the horizontal direction, the beam shaping plate 15 is displaced with respect to the block 163 such that the beam passing hole 151 of the beam shaping plate 15 is positioned so as not to shield the X-ray passing through the X-ray passing hole 164 by being superimposed on the X-ray passing hole 164.

The beam shaping plate 15 is displaced with respect to the block 163 such that the beam passing hole 151 of the beam shaping plate 15 is positioned so as to restrict the X-ray passing through the X-ray passing hole 164, whereby the X-ray cone beam can be radiated with spread width thereof in the horizontal direction that is limited more than the maximum spread width. In this manner, the spread of the X-ray cone beam in the horizontal direction is controlled by the position of the beam shaping plate 15.

Another beam shaping plate, though not shown, may be provided separately on the front or back side of the beam shaping plate 15. Specifically, there can be used a structure of, for example, the X-ray narrowing device that restricts an X-ray by a plurality of layered mask plates 4 and 5, which is disclosed in FIG. 4 of Japanese Utility Model Publication No. 7-15524 (1995) filed by the applicant of the present application.

Specifically, a beam passing hole having a predetermined shape is provided to another beam shaping plate such that the beam passing hole of the beam shaping plate in the horizontal direction has a width equal to or larger than the width of the beam passing hole 151 of the beam shaping plate 15 in the horizontal direction and that another beam shaping plate is displaceable relative to the beam shaping plate 15. The spread of the X-ray beam in the horizontal direction is controlled by controlling the positional relationship between the beam passing hole 151 and the beam passing hole of another beam shaping plate.

{X-Ray Generation Part 20}

Figure 7:
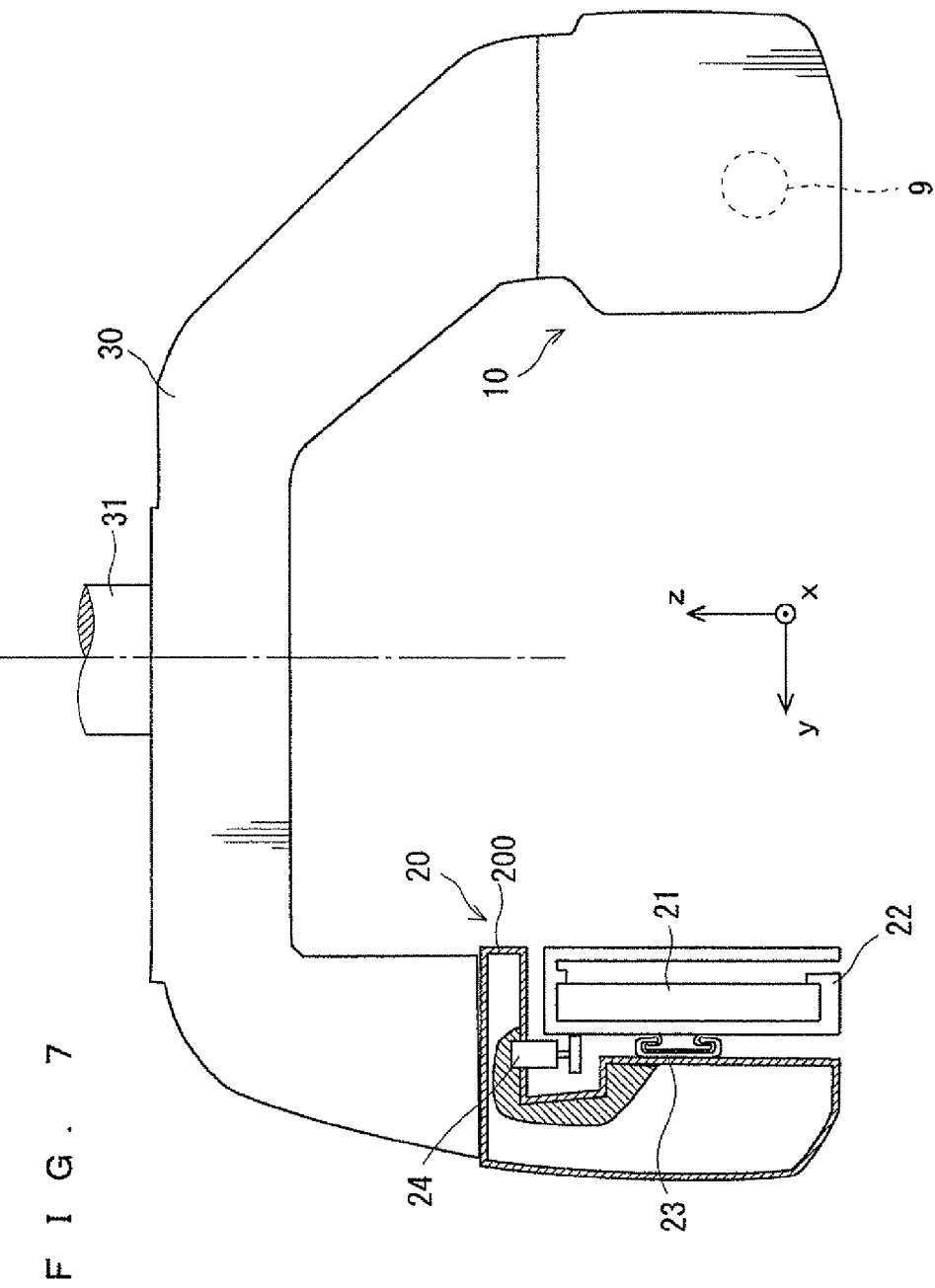
FIG. 7 is a front view showing the revolution arm.

FIG. 7 is a front view showing the revolution arm 30, which also partially shows the inside of the X-ray detection part 20. The X-ray detection part 20 includes a housing 200 for accommodating respective components of the X-ray detection part 20.

The housing 200 includes an X-ray detector 21 (an X-ray detector means) for detecting an X-ray, a detection holder 22 for holding the X-ray detector 21 therein, a guide rail 23 for supporting the detection holder 22 in a slidable manner in the horizontal direction, and a movement motor 24 mounted to the housing 200.

The X-ray detector 21 includes an X-ray sensor configured as a detection surface formed of semiconductor imaging elements, which are detection elements for detecting an X-ray, arranged into a two-dimensional plane in the longitudinal direction and the lateral direction. For example, a MOS sensor and a CCD sensor are conceivable as the X-ray sensor, which is not limited thereto, and various types including a flat panel detector (FPD) such as a CMOS sensor, X-ray image intensifier (XII) and other solid-state imaging elements are adoptable.

The detector holder 22 abuts against a roller attached to a rotation shaft of the movement motor 24. The detector holder 22 is driven by the movement motor 24 operating based on the control signal from the main-body control part 60 to be moved in the horizontal direction along the guide rail 23.

FIG. 8 is a perspective-view showing the detector holder 22. The detector holder 22 has beam passing holes (secondary shaping slits or collimators) 221 and 222 on the side opposed to the X-ray generation part 10. The beam passing holes 221 and 222 correspond to the shapes of the above-mentioned beam passing holes 151 and 152, respectively. For example, the X-ray cone beam passing through the beam passing hole 151 is shaped by the beam passing hole 221 at higher accuracy to be projected onto the X-ray detector 21.

It is also possible to omit the member having the beam passing holes 221 and 222.

The X-ray detector 21 includes a detection element group 211 and a detection element group 212. The detection element group 211 has imaging elements arranged in a rectangular shape so as to correspond to the beam passing hole 151 having an approximately rectangular shape. The detection element group 212 has imaging elements arranged in a vertically elongated manner so as to correspond to the beam passing hole 152 having a vertically elongated shape. The X-ray detector 21 is inserted into a slot 224 formed in the detection holder 22.

The X-ray detector 21 is set in the slot 224, whereby the detection element group 211 having an approximately square shape is positioned behind the beam passing hole 221 having an approximately rectangular shape, whereas the detection element group 212 is positioned behind the beam passing hole 222.

The movement of the detector holder 22 is controlled such that the detection element group 211 is positioned at the location where the X-ray that has passed through the beam passing hole 151 enters in X-ray CT imaging and that the detection element group 212 is positioned at the location irradiated with the X-ray that has passed though the beam passing hole 153 in panoramic imaging.

While the detection element groups 211 and 212 are provided in the X-ray detector 21 in the present embodiment, only the detection element group 211 may be provided such that an X-ray is detected by the same detection element group 211 merely by selection between the beam passing hole 151 and the beam passing hole 153 in X-ray CT imaging as well as panoramic imaging. On that occasion, an image signal is transmitted efficiently through the control so as to read the elements only within the range irradiated with an X-ray.

Figure 9:
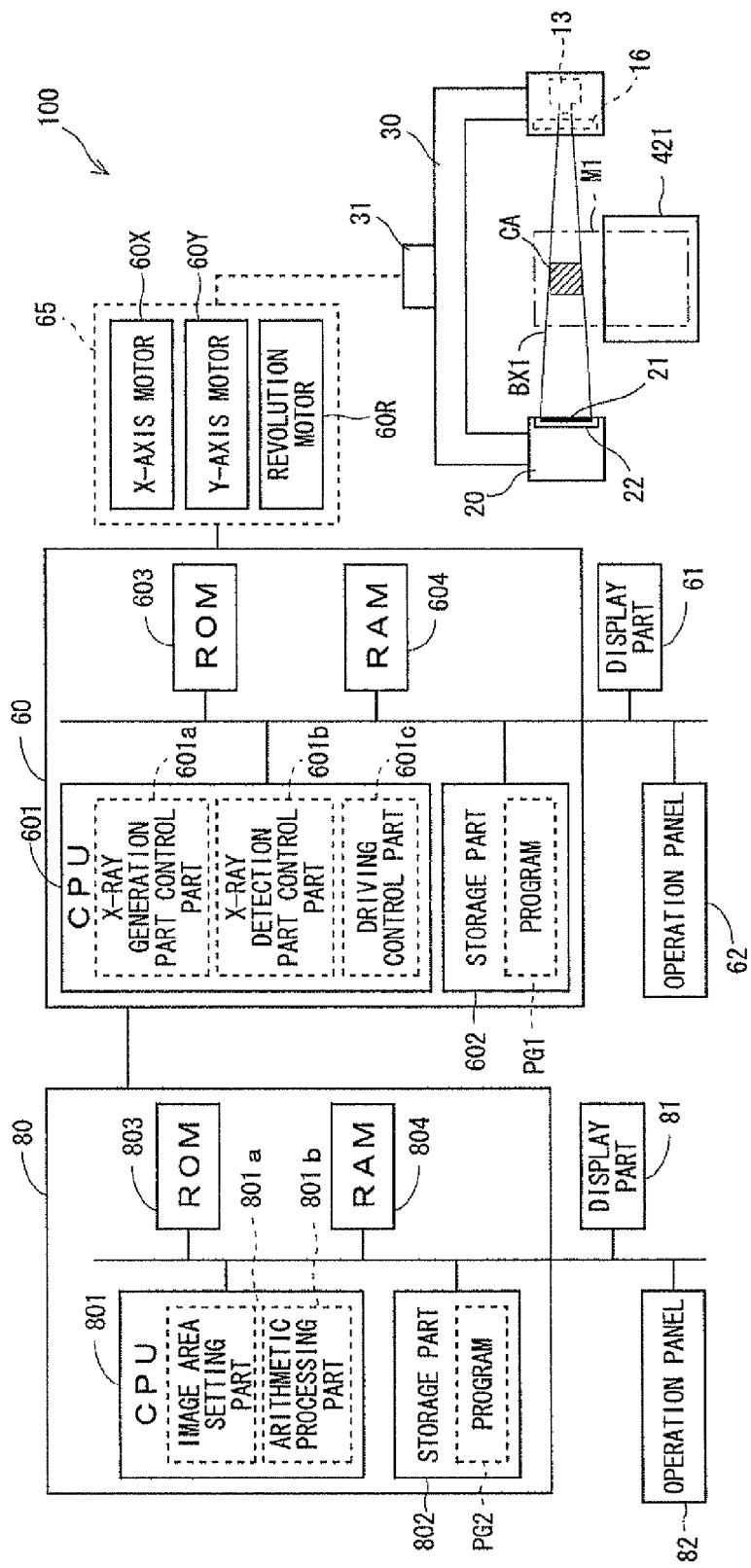
FIG. 9 is a block diagram showing a configuration of the X-ray imaging apparatus.

FIG. 9 is a block diagram showing the configuration of the X-ray imaging apparatus 100. As shown in FIG. 9, the revolution motor 60R, the X-axis motor 60X and the Y-axis motor 60Y form a driving part 65 for driving the revolution arm 30 relative to the object M1 located at a predetermined position. The driving part 65 and the object fixing part 421 function as a movement mechanism for moving the X-ray generation part 10 including the X-ray tube 9 and the X-ray detection part 20 including the X-ray detector 21 relative to the object M1. The driving part 65 and the object fixing part 421 are an example of a revolution driving part (a revolution driving means) in that the revolution arm 30 is driven in a revolving manner with the revolution motor 60R as a main element, which move the revolution arm 30 relative to the object M1 in a two dimensional plane perpendicular to the revolution shaft 31. In this respect, the driving part 65 and the object fixing part 421 are an example of a movement mechanism for moving the support part relative to the object M1 in a two-dimensional plane orthogonal (perpendicular) to the revolution shaft 31.

In the present embodiment, the revolution shaft 31 is attached to the horizontal movement mechanism configured as the XY-table 35 to move the revolution arm 30 in the horizontal direction with respect to the object M1. In another case, for example, the object fixing part 421 may be formed of a chair or the like and may be connected to the horizontal movement mechanism, to thereby move the object M1 relative to the revolution arm 30. Alternatively, each of the revolution shaft 31 and the object fixing part 421 may be provided with the horizontal movement mechanism so as to be movable in the horizontal direction. Still alternatively, one of the X-table and the Y-table may be provided to the object fixing part 421, while the other thereof may be provided to the revolution arm 30.

The main-body control part 60 has a configuration of a typical computer, in which a CPU 601, a storage part 602, a ROM 603 and a RAM 604 are connected to a bus line. The CPU 601 executes various control programs including a program PG1 for controlling the driving part 65, and the storage part 602 is formed as a fixed disk such as a hard disk and stores various data and the program PG1.

The CPU 601 executes the program PG1 stored in the storage part 602 on the RAM 604, and accordingly functions as an X-ray generation part control part 601a that controls the X-ray generation part 10 and an X-ray detection part control part 601b that controls the X-ray detection part 20 in accordance with various imaging modes. The X-ray generation part control part 601a is also capable of controlling an irradiation amount of X-rays and has the function of the X-ray irradiation control part (an X-ray irradiation control means). In addition, the CPU 601 functions as a driving control part 601c (a driving control means) that controls driving of the driving part 65 and, for example, controls driving such that, for example, the X-ray generation part 10 and the X-ray detection part 20 are moved in a track in accordance with various types of imaging.

The CPU 601 forming the main-body control part 60 and a CPU 801 forming the information processing main body 80 collectively constitute a control system.

The operation panel 62 connected to the main-body control part 60 is formed of a plurality of operation buttons or the like. As an input device used in place of the operation panel 62 or used together with the operation panel 62, a keyboard, a mouse, a touch pen and the like are used in addition to the operation button. Alternatively, recognition may be made upon reception of a voice command by a microphone or the like. That is, the operation panel 62 is just an example of the operation means. Therefore, any operation means may be adopted as long as the operation of the operator can be received. Still alternatively, it is possible to form the display part 61 of a touch panel and, in this case, the display part 61 has a part or the whole of the function of the operation panel 62.

Various information required for the operation of the main body unit 1 is displayed on the display part 61 in the format of a text, an image and the like. Note that the display contents displayed on the display part 81 of the information processing device 8 may be displayed also on the display part 61. Alternatively, various commands may be issued to the main body unit 1 through a pointer operation being performed on the text or the image displayed on the display part 61 by a mouse or the like.

The main body unit 1 locally takes an image of an area of interest of the object M1 (such as living organ, bones including teeth, and joint) in accordance with the operation panel 62 or the command from the information processing device 8. In addition, the main body unit 1 receives various commands, coordinate data and the like from the information processing device 8 and, on the other hand, transmits the X-ray projection data obtained by imaging to the information processing device 8.

The information processing main body 80 has a configuration of a typical computer, in which a CPU 801 that executes various programs, a storage part 802 that is formed of a fixed disk such as a hard disk and stores various data and a program PG2, a ROM 803 and a RAM 804 are connected to a bus line.

The CPU 801 executes the program PG2 stored in the storage part 802 on the RAM 804 to function as an image area setting part 801a and an arithmetic processing part 801b. The image area setting part 801a calculates the coordinates of the area designated by the operation part 82 to identify a CT image area CA, and the arithmetic processing part 801b performs arithmetic processing such as recreation of three-dimensional data from the projection data.

The programs PG1 and PG2 may be obtained by the main-body control part 60 or the information processing main body 80 via a predetermined network line or the like. Alternatively, the programs PG1 and PG2 stored in a portable medium (such as a CD-ROM) may be obtained by reading with a predetermined reader.

In the present embodiment, the operator designates the CT image area CA by the operation panel 62 or the operation part 82. Specifically, a screen (an illustration, a panoramic image or the like) displaying a part or the whole of a living body appears on the display part 61 or the display part 81, and the operator designates the area desired to be imaged by the operation panel 62 or the operation part 82, whereby the CT image area CA is designated. Alternatively, in place of displaying a screen for area designation, a desired portion may be designated directly by input of the name of the portion or a code by the operation panel 62 or the operation part 82.

A control part may be additionally provided in the operation panel 62 to bear a part of the control by the main-body control part 60, or the main-body control part 60 may be provided on the entire surface of the operation panel 62.

1.2. Outline of CT Imaging

Next, CT imaging performed by the X-ray imaging apparatus 100 including the above-mentioned components is described. The operation of the X-ray imaging apparatus 100 in CT imaging described below is achieved based on the control by the main-body control part 60 unless otherwise indicated.

FIG. 10 is a plan view conceptually showing the X-ray cone beam BX1. The X-ray beam emitted from the X-ray generator 13 (an X-ray generator means) is shaped into a pyramid shape (in this case, square pyramid shape) by the beam shaping plate 15, whereby the X-ray cone beam BX1 enters the X-ray detector 21. In CT imaging, an object is placed between the X-ray generation part 10 and the X-ray detection part 20, and the X-ray generation part 10 and the X-ray detection part 20 are revolved about the object. The revolution reference point CP is set on the optical axis CB of the X-ray cone beam BX1. The revolution reference point CP is described below. The optical axis CB is the center beam of the X-ray cone beam BX and serves as a symmetry axis of spreading of the X-ray cone beam BX in the x-direction.

Figure 12:
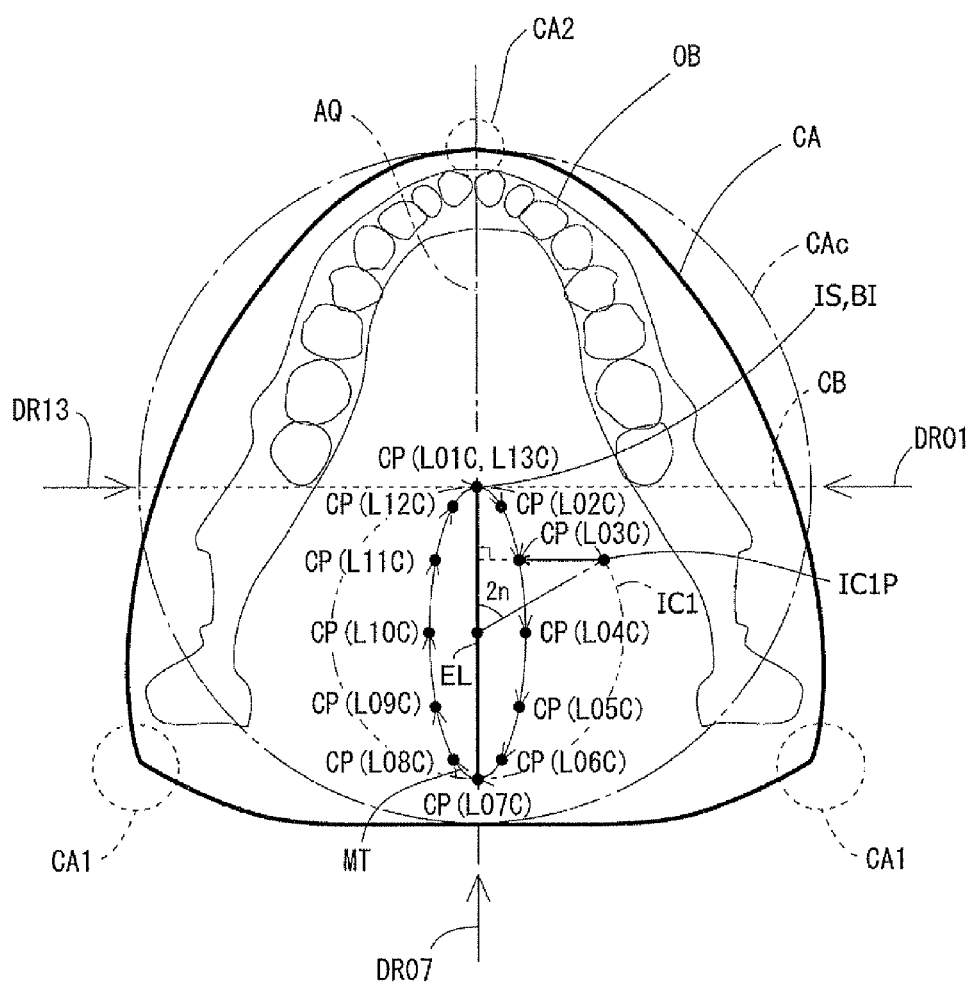
FIG. 12 is an enlarged plan view showing a moving trajectory of a revolution reference point and a CT image area shown in FIG. 11.

FIG. 11 is a plan view conceptually showing the state of imaging the image object OB. FIG. 12 is an enlarged plan view showing the moving trajectory of the revolution reference point CP and the CT image area CA shown in FIG. 11. In CT imaging shown in FIG. 11, the image object OB is the maxilla and mandible including all teeth. The jaw has a contour curved like an arch correspondingly to the shape of a dental arch. FIG. 11 shows the movements of the X-ray generator 13 from a location L01 to a location L13 by the rotation of the revolution arm 30 about the revolution shaft 31 for 180 degrees.

In addition, FIG. 11 shows the X-ray cone beams BX1 respectively emitted from the locations L01 to L13 of the X-ray generator 13 when the revolution arm 30 is rotated from the location L01 at 15-degree increments. More strictly, the locations L01 to L13 correspond to origins at which the X-ray of the X-ray tube 9 is generated, that is, the positions of the X-ray focal points. The X-ray generator 13 starts moving at the location L01 and finishes moving at the location L13 in CT imaging.

Traveling directions DR01 and DR13 of the optical axis CB being the center of the X-ray cone beam BX1 emitted from the location L01 intersect a symmetry axis AQ of the image object OB (jaw in this case). That is, the locations L01 and L13 are positioned just beside the image object OB. In other words, in CT imaging shown in FIG. 11, the X-ray generator 13 is moved from the right side of a head being an object to the left side of the head, passing through the rear. When the X-ray cone beam reaches the location L07 after the rotation for 90 degrees by the revolution of the revolution arm, a traveling direction DR07 of the optical axis CB of the X-ray cone beam BX1 emitted from the X-ray generator 13 is parallel to the symmetry axis AQ. In the example shown in FIG. 11, the symmetry axis AQ is a median line passing through the front and back of the jaw and also serves as the symmetry axis of the CT image area CA having an approximately triangular shape. The symmetry axis AQ passes through the top of the CT image area CA located at the point indicated by P1 in FIG. 11, where the top is opposed to the base of the CT image area CA having an approximately triangular shape.

When the X-ray generator 13 moves from the locations L01 to L13, the revolution reference point CP being a specific point set on the optical axis CB of the X-ray cone beam BX1 moves from a location L01C to a location L13C shown in FIG. 12. The locations L01C to L13C correspond to the locations L01 to L13 of the X-ray generator 13, respectively. In addition, the location L01C coincides with the location L13C, which is the intersection of the optical axis CB of the X-ray cone beam BX1 emitted from the location L01 or the location L13 and the symmetry axis AQ.

The X-ray imaging apparatus 100 collects projection data by the X-ray detection part 20 for a predetermined number of times while the X-ray cone beam BX1 is revolved by the rotation of the revolution shaft 31. Specifically, the main-body control part 60 monitors the revolution motor 60R, and the X-ray detection projection data of the X-ray detector 21 is collected as projection data every time the support part 300 (that is, revolution arm 30 that is revolved about the revolution shaft 31) is rotated for an amount of a predetermined angle. During the revolution of the support part 300, the X-ray cone beam BX1 may be radiated to the object all the time, or the X-ray cone beam BX1 may be radiated in accordance with the timing at which the X-ray detection part 20 intermittently detects an X-ray. In the latter case, an X-ray is intermittently radiated to the object M1, which reduces an X-ray exposure amount of the object.

The collected projection data is sequentially transferred to the information processing device 8 and is stored in, for example, the storage part 802. Then, the collected projection data is processed by the arithmetic processing part 801*b* to be recreated into three-dimensional data. The arithmetic processing of recreation by the arithmetic processing part 801*b* includes predetermined preprocessing, filter processing and back projection processing. Various arithmetic processing technologies including a well-known technology are applicable to the arithmetic processing.

In CT imaging shown in FIG. 11, the X-ray cone beam BX1 is radiated while revolving the support part 300 that supports the X-ray generation part 10 and the X-ray detection part 20, to thereby perform imaging of the CT image area CA being the area of interest, where the revolution motor 60R for the revolution shaft 31, the X-axis motor 60A and the Y-axis motor 60Y are controlled in a cooperative (interlocking) manner such that the CT image area CA has an approximately triangular shape. The approximately triangular shape is, for example, a triangular shape.

The CT image area is an area targeted to be irradiated with an X-ray in CT imaging, which is an area irradiated with an X-ray sufficient for recreating an object located in the CT image area in three-dimensional data from the X-ray transparent data or projection data of the CT image area, without causing any problem. In that sense, the CT image area is a target recreation area. Recreation is performed by, for example, back projection. In terms of control, normally, an X-ray is irradiated and an X-ray transparent data is obtained in a consecutive manner while CT imaging of the CT image area is performed by the revolution of the support part 300. Desirably, projection data for 180 degrees or more is obtained at all points in the CT image area.

Description is now given of the control of movements of the X-ray cone beam BX1 with respect to the object for obtaining the CT image area CA having an approximately triangular shape. As shown in FIG. 11, in a case where the X-ray generator 13 moves from the location L01 to the location L13 during CT imaging, the revolution arm 30 that rotates about the revolution shaft 31 is rotated for 180 degrees, so that the traveling direction of the optical axis CB of the X-ray cone beam BX1 is rotated for 180 degrees. For example, in the case shown in FIG. 11, the traveling direction of the optical axis CB is rotated from the direction DR01 to the direction DR13 for 180 degrees. As shown in FIG. 12, the X-ray cone beam BX1 is moved such that the revolution reference point CP moves so as to generate an oval trajectory, simultaneously with the rotation of the revolution arm 30.

More specifically, the revolution reference point CP starts from the location L01C, moves to the locations L02C, L03C, L04C . . . in order, and returns to the starting location L01C again during the rotation of the revolution shaft 31 for 180 degrees. That is, the revolution reference point CP goes round of an oval shape while the revolution arm 30 is rotated for 180 degrees. The revolution reference point CP is allowed to be moved by the movement of the revolution shaft 31 through driving-control of the X-axis motor 60X and the Y-axis motor 60Y.

With respect to the X-ray detector 21, as shown in FIG. 11, the X-ray detector 21 forms an arc-shaped trajectory having an approximately semi-circular shape that moves at least from one to the other of the right and left of the target image area (area of interest including the image object OB) during CT imaging. In the case shown in FIG. 11, the X-ray detector 21 forms the trajectory moving from the right to the left with respect to the center of a human head being the object M1, that is, the trajectory moving from the right to the left opposed to each other with the symmetry axis AQ therebetween.

In the arc-shaped trajectory having an approximately semi-circular shape, attention is given to the positional relationship between the case where the X-ray detector 21 is positioned at any of the right and left locations (that is, the case where the X-ray generator 13 is positioned at any of the locations L01 and L013) and the case where the X-ray detector 21 is positioned in the middle of the right and left sides (that is, the case where the X-ray generator 13 and the X-ray detector 21 are positioned at the location L07 on the symmetry axis AQ, which is the center location). In this case, a distance 11, 13 between the X-ray detector 21 and the target image area when the X-ray detector 21 is positioned at any of the right and left sides is larger than a distance 12 between the X-ray detector 21 and the target image area when the X-ray detector 21 is positioned at the center.

Note that the "distance between the target image area and the X-ray detector 21" is the distance between one point in the area of interest that is the target image area and the center portion of the detection surface of the X-ray detector. For example, this corresponds to the distance between one point in the center of the jaw (or a dental arch) being an area of interest and the center portion of the detection surface of the X-ray detector 21.

Taken as a specific example of one point at the center of the jaw (or a dental arch) being an area of interest is, for example, a spot corresponding to an intersection IS of the symmetry axis AQ and the optical axis CB directed toward the direction DR01 in the state in which the X-ray generator 13 is positioned at the location L01. The intersection IS also corresponds to an intersection of the symmetry axis AQ and the optical axis CB directed toward the direction DR13 in the state in which the X-ray generator 13 is positioned at the location L13.

Alternatively, the distance between the target image area and the X-ray detector 21 may be taken as the distance between the X-ray detector 21 and the edge of the area of interest being the target image area. A distance 14, 16 between the X-ray detector 21 and the target image area when the X-ray detector 21 is positioned on any of the right and left is larger than a distance 15 between the X-ray detector 21 and the target image area when the X-ray detector 21 is positioned at the center. On this occasion, the location of the edge of the target image area may be considered as the location of the edge on the optical axis CB.

More strictly, the distance 14, 16 is the distance between the detection surface of the X-ray detector 21 and any of the right and left ends of the target image area, which is closer to the X-ray detector 21, when the X-ray detector 21 is positioned at any of the right and left locations. The distance 15 is the distance between the detection surface of the X-ray detector 21 and the top of the CT image area CA located at the point indicated by P1 being opposed to the base of the target image area when the X-ray detector 21 is positioned at the symmetry axis AQ.

As shown in FIG. 12, the CT image area CA set in the present embodiment has a symmetrical shape obtained by connecting extending parts CA1, CA1 protruding outwardly to the right and left and a top CA2 by a curved line so that the CT image area CA protrudes toward the extending parts CA1, CA1 and toward the top CA2 upwardly from the extending parts CA1, CA1 on the right and left of the base, where vertical and horizontal sides comply with those of FIG. 12. In other words, assuming that the CT image area CA is an imaginary triangle with the extending parts CA1, CA1 and the top CA2 being three vertices, the CT image area CA has a shape in which three sides of the triangle are each expanded outwardly.

As described above, in the present embodiment, an X-ray exposure amount for the object can be reduced in a case where the CT image area CA is formed approximately into a triangular shape, strictly, in a case where the CT image area CA seen from a direction which is parallel to the axis direction of the revolution shaft 31 (place surface apparently) is formed approximately into a triangular shape, such that CT imaging is targeted for the area of interest including an approximately semi-circular-shaped (also approximately semi-oval shaped) image object OB having an arch shape such as a jaw.

Although the revolution reference point CP is set at the position of the revolution shaft 31 in some cases, the revolution reference point CP may be set at any location other than that of the revolution shaft 31. The shape and size of the CT image area CA vary in accordance with the set location of the revolution reference point CP on the optical axis CB of the X-ray cone beam BX1 and the shape of the moving trajectory of the revolution reference point CP, and thus parameters thereof are appropriately changed by for example, the shape and size of the image object OB. While the extending direction of the axis AQ is the longitudinal axis direction of a trajectory MT in the present embodiment, a case where the direction perpendicular to the axis AQ is the longitudinal direction of the trajectory MT is also conceivable.

While the X-ray imaging apparatus according to the present embodiment can perform CT imaging such that the CT image area CA has an approximately triangular shape as described above, this X-ray imaging apparatus can also perform general X-ray CT imaging in which CT imaging is performed through revolutions of the X-ray generator 13 and the X-ray detector 21 about the fixed revolution center, with the location of the revolution shaft 31 being fixed during X-ray CT imaging.

Further, as disclosed in Japanese Patent Application Laid-Open No. 2007-29168 filed by the applicant of the present application, general X-ray CT imaging can be performed by revolving the revolution arm 30 while rotating the revolution shaft 31 about the center of the area of interest, with the revolution center in imaging being fixed. Each imaging can be performed by mode switching (CT imaging mode for an approximately triangular-shaped CT image area, CT imaging mode with a fixed revolution axis and CT imaging mode with a fixed revolution center in imaging). This is described below in detail.

The above-mentioned CT image area CA having an approximately triangular shape may be limited to only the maxilla range or may be limited to only the mandible range. Needless to say, the CT image area CA may be limited to the area including both of the maxilla and mandible. In a case where the CT image area CA is limited to only the maxilla range, the X-ray cone beam is radiated to only the maxilla portion during X-ray CT imaging. While, in a case where the CT image area CA is limited to only the mandible range, the X-ray cone beam is radiated to only the mandible portion during X-ray CT imaging. Further, in the case where the CT image area CA is limited to the area including both of the maxilla and mandible, the X-ray cone beam is radiated to the range including both of the maxilla and mandible during X-ray CT imaging. The irradiation is adjusted by the above-mentioned vertical beam shaping mechanism.

The revolution reference point CP is now described. In order to achieve CT imaging for an approximately triangular-shaped CT image area with the configuration described here, it suffices that the movements of the X-ray generator 13 and the X-ray detector 21 are controlled so as to follow the track as shown in FIG. 11. In order to perform such CT imaging, therefore, a mechanical movement is controlled in the present embodiment as described below. Control based on coordinate operation is appropriate for the mechanical movement control. The revolution reference point CP shown in FIG. 11 is set as a reference point of the coordinate operation.

As described above, setting is made such that the revolution reference point CP goes round of the oval-shaped trajectory MT while the revolution shaft 31 is rotated for 180 degrees from the location L01 to the location L13. Further, in X-ray CT imaging shown in FIG. 12, when an imaginary circle IC having a diameter of the length of the trajectory MT along the axis AQ (here, longitudinal axis EL of the oval trajectory MT) is assumed, control is made such that, when the revolution shaft 31 is rotated for n-degrees from the state in which the X-ray generator 13 is positioned at the location L01, the revolution reference point CP is moved to the place (in the example shown in FIG. 12, location L03C) at which the straight line extended so as to intersect the axis AQ from a point IC1P on the imaginary circle IC1 at which the revolution reference point CP advances for 2n-degrees from the location L01C intersects the oval trajectory MT. That is, in the example shown in FIG. 11 and FIG. 12, the revolution reference point CP is moved such that an orthogonal projection of the revolution reference point CP on the axis AQ produces a simple harmonic motion. The speed of motion of the revolution reference point CP is not limited to a variable one as described above. It suffices that the revolution reference point CP moves from the location L01C to reach the location L07C while the X-ray generator 13 moves from location L01 to the location L07 and that the revolution reference point CP moves from the location L07C to reach the location L13C while the X-ray generator 13 moves from the location L07 to the location L13.

Description is now given with reference to FIG. 12. In the state in which the X-ray generator 13 is positioned at the location L01 shown in FIG. 11, the optical axis CB passes through the center of the area of interest. In CT imaging conventionally performed, CT imaging is performed by fixing the revolution center of the X-ray generator 13 and the X-ray detector 21 to the intersection IS of the symmetry axis AQ and the center of the area of interest, for example, the optical axis CB in the state in which the X-ray generator 13 is positioned at the location L01. The CT image area of this conventional CT imaging is a circular CT image area CAc with the intersection IS being the center of a circle.

The reason for the above is as follows. Assuming that the front teeth are always included in the CT image area, in order to achieve an X-ray imaging apparatus available at an appropriate price, which is caused to perform CT imaging of teeth as much as possible, it is required to use an X-ray detector having a detection surface of a somewhat limited size. This necessitates the use of an X-ray detector having a detection surface of a size as to perform X-ray imaging in the range of the CT image area CAc shown in FIG. 12.

In performing coordinate operation of the configuration described above, attention is paid to a location BI overlapping the intersection IS on the optical axis CB, and the location BI is set as the revolution reference point CP. In conventional CT imaging, the X-ray generator 13 and the X-ray detector 21 are revolved about the intersection IS overlapping the location BI. In this sense, the location BI is the revolution center of the X-ray cone beam. In the case of the configuration described above, the location of the revolution reference point CP is moved in accordance with the revolution angle of the revolution arm 30. The trajectory thereof is indicated by the locations L01C to L12C in FIG. 12.

The location of the revolution reference point CP is determined by coordinate operation for every revolution angle of the revolution arm 30. The mechanical movement of the revolution arm 30 is controlled based on the coordinate operation. When a reference point to be noted is determined in performing coordinate operation, the method in which attention is paid to the location BI as described above is adopted. This means that the method of setting the above-mentioned location BI as the revolution reference point CP is adopted.

While the location BI is conceivable as one point of the X-ray cone beam BX1, it is conceivable as one point of the revolution arm 30 because the location of the X-ray cone beam BX1 in the revolution arm 30 is determined.

The most important thing in determining the moving trajectory MT of the revolution reference point CP is that the X-ray detector 21 is set so as to be close to the point of the intersection IS when the X-ray generator 13 is positioned at the location L07.

A jaw is expanded outwardly at the portions of the right and left jaw joints on the rear side. In a case where the right and left jaw joints are both fit in the irradiation range of the X-ray cone beam BX1 having a limited spreading width when the X-ray cone beam BX1 is radiated from the rear of the head toward the front of the head, it is advantageous that the X-ray detector 21 is close to the target image area. Therefore, the location L07C of FIG. 12 is set to the location at which the X-ray detector 21 is close to the intersection IS.

In order to achieve the configuration of the present embodiment, the revolution reference point CP is set because it is convenient to determine the above-mentioned revolution reference point CP and provide movement control information to the driving part 65 in terms of coordinate operation. Alternatively, the configuration of the present embodiment may be achieved with a mechanical configuration. For example, the movement mechanism of the revolution shaft 31 having the structure of a well-known oval ruler may be used to achieve the configuration of the present embodiment mechanically by movements of the revolution shaft 31.

Figure 13:
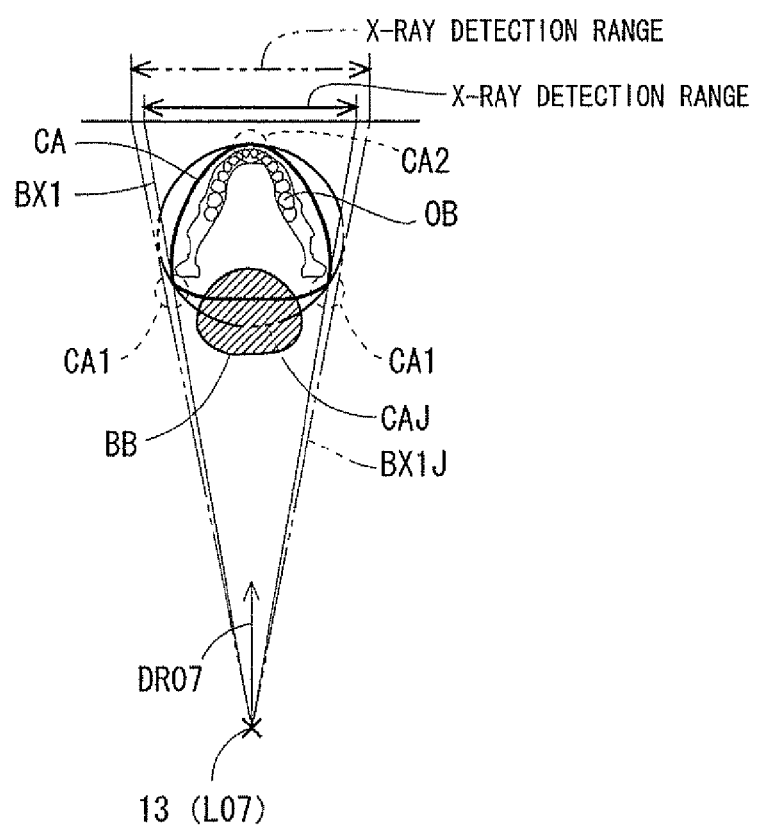
FIG. 13 is a plan view showing a comparison between a case where the CT image area has a circular shape and a case where the CT image area has an approximately triangular shape.

FIG. 13 is a plan view showing the comparison between the case of the circular CT image area CA and the approximately triangular CT image area CA. The state in which the X-ray generator 13 is positioned at the location L07 in FIG. 11 is assumed here. In conventional CT imaging in which the revolution center of the X-ray generator 13 and the X-ray detector 21 is fixed, when a CT image area CAJ has a circular shape including all areas of interest including the image object OB as shown in FIG. 13 so as to set the entire area of the image object OB as the CT image area, an X-ray of an X-ray cone beam BX1J is radiated to a wider range compared with the X-ray cone beam BX1 according to the present embodiment.

Accordingly, in the case where the CT image area CA having an approximately triangular shape is set as in the present embodiment, the detection range of an X-ray by the X-ray detector 21 is smaller as shown in FIG. 13 compared with the case where the CT image area CAJ having a circular shape is set. Therefore, the detection surface of the X-ray detector 21 can be made smaller in size according to the present embodiment, which enables to reduce a device cost.

Although the cervical spine BB is located behind the jaw as shown in FIG. 13, the CT image area is approximately triangular in shape. This means that the base portion of an approximately triangular shape is positioned inside the CT image area CAJ having a circular shape, and it is revealed that an X-ray exposure amount in the cervical spine BB region can be reduced.

Further, as is apparent from the comparison between the X-ray cone beams BX1 and BX1J, as a result of the CT image area CA being formed into an approximately triangular shape as in the present embodiment, the range in which an X-ray is radiated can be narrowed more compared with the case where the CT image area CA is formed into a circular shape.

As described above, as to the jaw including a dental arch being the image object OB, the CT image area CA is formed into an approximately triangular shape, whereby a curbed jaw is accommodated within a curved line that is connected such that the right and left jaw joints are accommodated in the portions in the vicinity of the right and left extending parts CA1, CA1, that the front teeth are accommodated in the portion in the vicinity of the top CA2, and that the CT image area CA protrudes from the right and left extending parts CA1, CA1 toward the top CA2. On the other hand, in the case where the circular CT image area CAJ is set, the area extending beyond the jaw portion is relatively larger compared with the case where the CT image area CA is formed into an approximately triangular shape. Accordingly, the X-ray radiation to the portion other than the image object OB can be reduced, leading to a reduction of the X-ray exposure amount for the object.

1.2.1. Acquisition of Projection Data for 180 Degrees

It is possible to obtain a CT image of image quality to such an extent that no trouble is caused to diagnosis merely by revolving the X-ray cone beam BX1 for just 180 degrees as shown in, for example, FIG. 11. As shown in FIG. 11, however, at a intersection P1 (point corresponding to the top CA2 of the CT image area CA) of the right outer edge of the X-ray cone beam BX1 emitted from the location L01 and the left outer edge of the X-ray cone beam BX1 emitted from the location L13, an X-ray can be radiated only within the range smaller than 180 degrees (specifically, range of an angle obtained by subtracting a fan angle θ1 of the X-ray cone beam from 180 degrees). As described above, points that can be irradiated with an X-ray only within the range of less than 180 degrees are positioned on the side closer to the intersection P1 with respect to the straight line connecting the location L01 and the location 13 in the CT image area CA. The projection data for 180 degrees cannot be obtained as to those points. In order to generate a highly accurate CT image, it is desirable to obtain the projection data for 180 degrees as to the entire CT image area CA, and a CT image having higher definition can be generated if the projection data for 180 degrees is obtained. Description is now given of the configuration example for obtaining the projection data for 180 degrees in the entire CT image area CA with reference to FIGS. 14A and 14B.

Figure 14A:
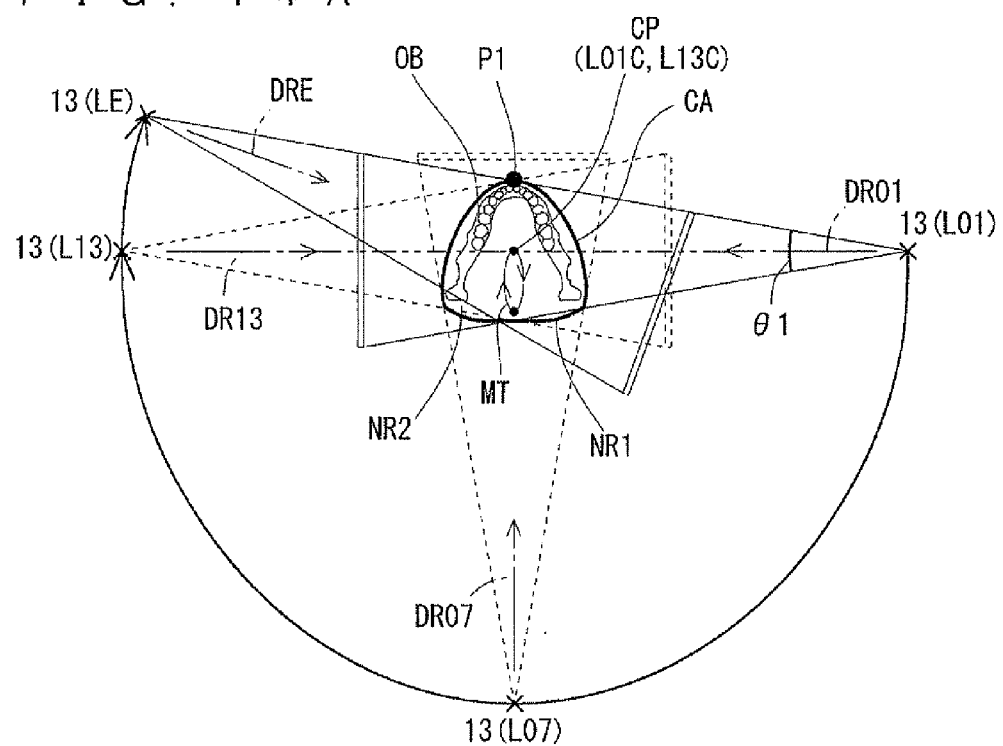
FIGS. 14A and 14B are views for describing CT imaging in which the X-ray cone beam is revolved for an amount obtained by adding a fan angle to 180 degrees.
Figure 14B:
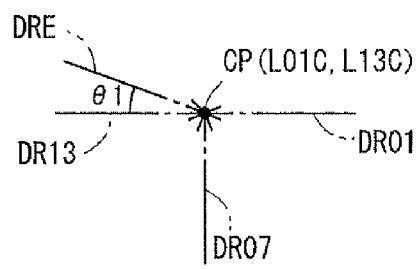

FIGS. 14A and 14B are views for describing CT imaging for revolving the X-ray cone beam BX1 for an amount obtained by adding the fan angle θ1 to 180 degrees in the revolution direction. FIG. 14A is a plan view showing the state of CT imaging, and FIG. 14B shows the traveling directions of the optical axis CB of the X-ray cone beam BX1 respectively emitted from the locations L01, L07, L13 and LE. As shown in FIG. 14A, the fan angle refers to an angle θ1 of broadening of the X-ray cone beam BX1 in a plane intersecting the revolution shaft 31 (in this case, a two-dimensional plane perpendicular to the revolution shaft 31).

In CT imaging shown in FIG. 14A, the X-ray imaging apparatus 100 moves the X-ray generator 13 while revolving from the location L01 to the location L13, and then controls the X-axis motor 60X, the Y-axis motor 60Y and the revolution motor 60R in a cooperative (interlocking) manner so as to rotate the revolution shaft 31 for the fan angle θ1 while retaining the revolution reference point CP of the X-ray cone beam BX1 at the location L13C. As a result, the X-ray generator 13 is moved while rotating from the location L13 to the location LE in an oval arc shape. Alternatively, the X-ray generator 13 is moved while revolving from the location L01 to the location L13, and then the revolution reference point CP of the X-ray cone beam BX1 may be continuously traveling in the oval track in an arrow direction shown in FIG. 14A.

As shown in FIG. 14B, the angle formed by the direction DR01 and the direction DR13 is 180 degrees, and the angle formed by the direction DR13 and a direction DRE is θ1 (=fan angle). That is, the traveling direction of the optical axis CB of the X-ray cone beam BX1 is rotated about the location L01C (=location L13C) from the direction DR1 to the direction DRE for an amount obtained by adding the fan angle θ1 to 180 degrees.

The X-ray cone beam BX1 is rotated for the amount of (180 degrees+fan angle θ1) in this manner, whereby it is possible to obtain the projection data in which an X-ray is radiated from the respective directions within the range of 180 degrees for all points of the CT image area. In particular, as shown in FIG. 14A, the right outer edge of the X-ray cone beam BX1 emitted from the location L01 and the left outer edge of the X-ray cone beam emitted from the location LE overlap each other in a parallel manner, which reveals that the projection data in which an X-ray is radiated from respective directions within the range of 180 degrees can be obtained for the intersection P1.

Needless to say, the revolving range of the X-ray cone beam BX1 can be appropriately set between 180 degrees or more and less than 360 degrees. The revolving range of the X-ray cone beam BX1 may be set by an integral multiple of 45 degrees such as 225 degrees, 270 degrees and 315 degrees, may be set by an integral multiple of 60 degrees such as 180 degrees, 240 degrees and 300 degrees, or may be set to angles of round numbers, for example, by an integral multiple of 50 degrees such as 200 degrees, 250 degrees, 300 degrees and 350 degrees. The revolving range of the X-ray cone beam BX1 can be appropriately set by, for example, a degree of sharpness of a generated CT image in terms of the structure of an X-ray imaging apparatus, the control method therefor and arithmetic operation.

The CT image area CA being the target image area is not limited to the area that is always irradiated with an X-ray in CT imaging. In the CT image area CA shown in FIG. 14A, for example, there is a non-irradiation area NR1 that is not irradiated with the X-ray cone beam BX1 emitted from the location L01. In addition, there is a non-irradiation area NR2 that is not irradiated with the X-ray cone beam BX1 emitted from the location LE. On the other hand, those areas are irradiated with X-rays from the directions within the range of 180 degrees in CT imaging while the X-ray generator 13 is moved from the location L01 to the location LE. That is, while the non-irradiation areas NR1 and NR2 are not always irradiated with X-rays in CT imaging, projection data for 180 degrees can be obtained in those areas, and thus CT images can be generated well in those areas.

Further, there is the portion irradiated with an X-ray from the direction beyond 180 degrees in the CT image area CA shown in FIG. 14A. For example, the location L01C is irradiated with an X-ray in the direction DR13 from the side opposite to the X-ray in the direction DR01 by 180 degrees, and is further irradiated with an X-ray in the direction DRE where the revolution shaft 31 is rotated from the direction DR13 by the fan angle θ1. That is, an X-ray is irradiated additionally by the fan angle θ1 beyond the range of 180 degrees at the location L01C (see FIG. 14B). Therefore, in the area in which an X-ray is radiated beyond 180 degrees, an X-ray may be controlled to be radiated for just 180 degrees by variable adjustment of the fan angle of the X-ray cone beam BX1 during the start and end of X-ray irradiation. As a result, an object can be imaged by a required amount of X-rays, which reduces the X-ray exposure amount of the object.

In CT imaging shown in FIG. 14A, revolution imaging with the X-ray cone beam BX1 is performed for 180 degrees (180-degree-revolution imaging) in which the X-ray generator 13 is moved from the location L01 to the location L13, and then revolution imaging is performed for the fan angle θ1 (fan-angle-revolution imaging). The 180-degree-revolution imaging causes the revolution reference point CP to move in an oval manner. The execution order of 180-degree-revolution imaging and fan-angle-revolution imaging is not limited thereto, and fan-angle-revolution imaging may be performed before 180-degree-revolution imaging is performed. In this case, the X-ray generator 13 starts revolving from the side short of the location L01, and fan-angle-revolution imaging is performed until the X-ray generator 13 reaches the location L01. Then, the X-ray generator 13 is moved from the location L01 to the location L13, whereby CT imaging is finished.

1.2.2. Adjustment of X-Ray Amount

FIGS. 15A, 15B, 15C, 15D and 15E are figures for describing the state in which an X-ray amount radiated to the object is adjusted during CT imaging shown in FIG. 14A. Note that FIGS. 15A, 15B and 15C are plan views showing the positional relationships between the X-ray cone beams BX1 emitted from the locations L04, L07 and L11 and the cervical spine BB in the body of the object. FIG. 15D shows the plot of the intensity of X-ray output, where a vertical axis and a horizontal axis represent the X-ray output intensity and revolution angle, respectively. FIG. 15E shows the plot of the revolution speed of the X-ray cone beam BX1, where a vertical axis and a horizontal axis represent the revolution speed and revolution angle, respectively. FIGS. 15D and 15E show the rotation angle of the revolution shaft 31 as the revolution angle, with the rotation angle of the revolution shaft 31 being 0 degrees when the X-ray generator 13 is positioned at the location L01. The distance between the dental arch and cervical spine of an actual human body is not large as shown in FIGS. 15A, 15B and 15C, which is exaggerated for easy understanding.

In a case where the image object OB is a jaw including a dental arch, the cervical spine BB being the X-ray absorbing portion is located behind the jaw inside the object. It is preferable in CT imaging that an X-ray amount be controlled in a case including the state in which an X-ray passes through the above-mentioned X-ray absorbing portion to reach the image object OB as well as the state in which an X-ray reaches the image object OB as it is without passing through the X-ray absorbing portion.

As shown in FIGS. 15A and 15C, for example, in the state in which the X-ray generator 13 is positioned at the locations L04 and L10, the X-ray cone beam BX1 does not overlap the cervical spine BB which easily absorbs an X-ray. Therefore, good projection data of the CT image area CA can be obtained even with a relatively small X-ray amount. As shown in FIG. 15B, however, in the state in which the X-ray generator 13 is positioned at the location L07 (location behind the object), the X-ray cone beam BX1 entirely overlaps the cervical spine BB, and thus the X-ray that has passed through the cervical spine BB reaches the CT image area CA. Therefore, a relatively large amount of X-rays is radiated preferably in this state temporarily for obtaining good projection data of the CT image area CA.

In this manner, an X-ray amount is changed in accordance with the positional relationship between the X-ray cone beam BX1 and the X-ray absorbing portion such as the cervical spine BB, that is, in accordance with the revolution angle of the revolution arm 31, and accordingly in the present embodiment, any one of the X-ray output and revolution speed is preferably adjusted as shown in FIG. 15D or FIG. 15E.

For example, in a case where an X-ray output is adjusted, as shown in FIG. 15D, control is made such that an X-ray amount output from the X-ray generator 13 is larger in the state of FIG. 15B compared with the states of FIGS. 15A and 15C. In a case where the revolution speed is adjusted, as shown in FIG. 15E, control is made such that the revolution speed (revolution speed of the revolution arm 30) is made slower in the state of FIG. 15B compared with the states of FIGS. 15A and 15C, to thereby relatively increase the X-ray amount to the CT image area CA.

Even if there is a portion having relatively high X-ray absorption, it is possible to perform, through the above-mentioned control, CT imaging in which an effect thereof is mitigated, whereby a good CT image can be obtained. As to the adjustment of an X-ray amount shown in FIGS. 15A, 15B, 15C, 15D and 15E, there can be used various technologies including the technology disclosed in Japanese Patent Application Laid-Open No. 2010-75682.

1.3. Other CT Imaging 1

In CT imaging shown in FIG. 14A, the revolution reference point CP is retained at the location L13C in fan-angle-revolution imaging in which the X-ray generator 13 is moved from the location L13 to the location LE. As described above, however, a good CT image of the CT image area CA can be generated when the projection data for 180 degrees is obtained. Therefore, the revolution reference point CP may be moved to an appropriate location in fan-angle-revolution imaging as long as the projection data for 180 degrees can be obtained.

FIG. 16 is a plan view showing an outline of other CT imaging. In CT imaging shown in FIG. 16, the revolution reference point CP is moved such that the X-ray cone beam BX1 is radiated to the entire CT image area CA having an approximately triangular shape in fan-angle-revolution imaging. Accordingly, the X-ray generator 13 is moved so as to go apart from the CT image area CA and toward a location LEs (in other words, the X-ray detector 21 is moved close to the CT image area CA). In CT imaging as described above, the projection data in which the entire CT image area CA is irradiated with an X-ray can be obtained, and thus such CT imaging is effective in recreation of three-dimensional data. Note that as to the non-irradiation area NR2, the projection data for 180 degrees has been obtained in 180-degree-revolution imaging as described above, and thus it is possible to obtain a sufficiently highly-accurate CT image without moving the revolution reference point CP.

1.4. Other CT Imaging 2

While fan-angle-revolution imaging is performed after the completion of 180-degree-revolution imaging in CT imaging shown in FIG. 14A, fan-angle-revolution imaging may be performed separately before and after 180-degree-revolution imaging.

Figure 17A:
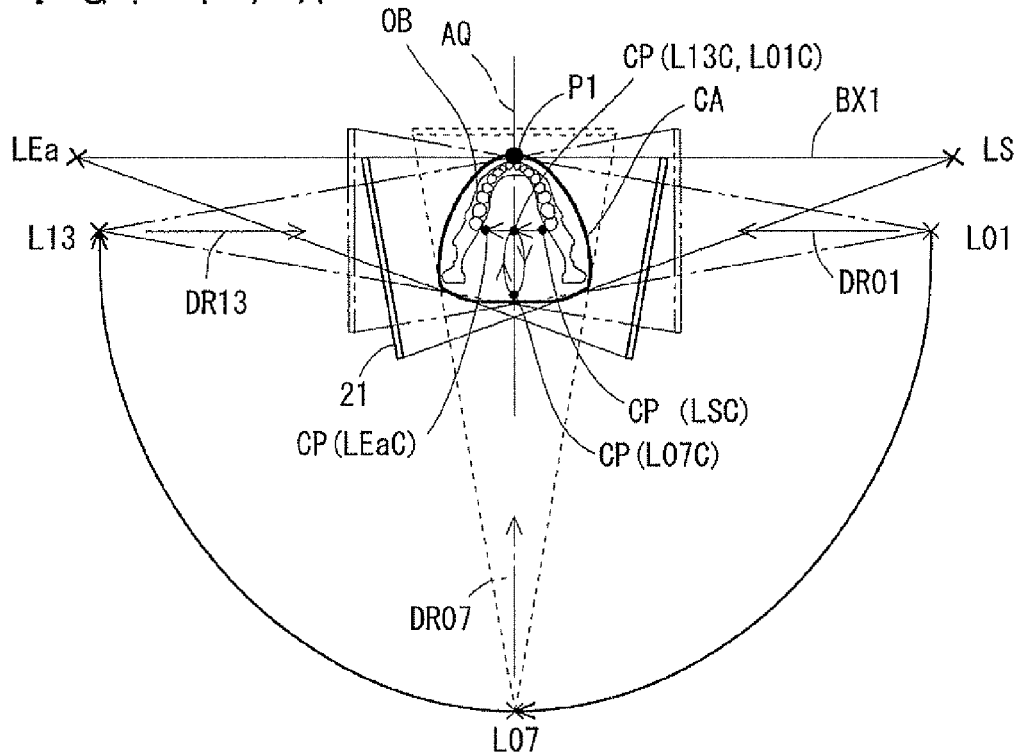
FIGS. 17A and 17B are views for describing an outline of other CT imaging.
Figure 17B:
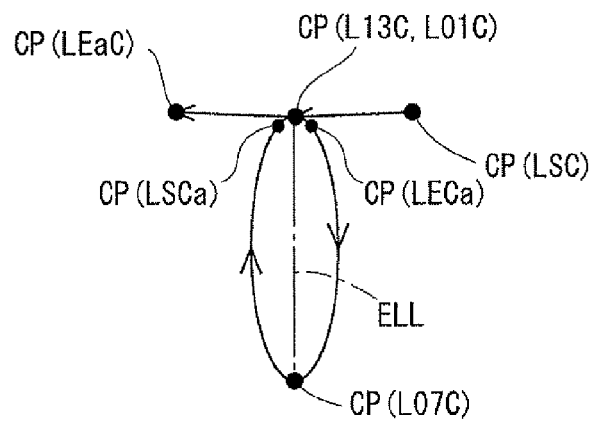

FIGS. 17A and 17B are views for describing an outline of other CT imaging. FIG. 17A is a plane view showing the state of imaging the CT image area CA, while FIG. 17B is an enlarged view showing the moving trajectory of the revolution reference point CP shown in FIG. 17A.

In CT imaging shown in FIG. 17A, the X-ray imaging apparatus 100 starts CT imaging from the location LS short of the location L01, moves the X-ray generator 13 from the locations L01, L02 ... L12 and L13, then further moves the X-ray generator 13 to a location LEa, and finishes CT imaging. The position coordinates of the locations LS and LEa are respectively set such that the right outer edge of the X-ray cone beam BX1 emitted from the location LS overlaps the left outer edge of the X-ray cone beam BX1 emitted from the location LEa in a parallel manner.

In particular, in CT imaging shown in FIGS. 17A and 17B, the revolution shaft 31 is revolved for an angle amount of the half the fan angle θ1 ((θ1)/2) while the X-ray generator 13 is moved from the location LS to the location L01 and while the X-ray generator 13 is moved from the location L13 to reach the location LEa. That is, it is considered that imaging corresponding to fan-angle-revolution imaging of CT imaging shown in FIG. 14A is performed evenly before and after 180-degree-revolution imaging in a separate manner.

In CT imaging shown in FIGS. 17A and 17B, the X-ray imaging apparatus 100 moves the X-ray generator 13 during imaging corresponding to fan-angle-revolution imaging such that the X-ray cone beam BX1 is radiated to the entire CT image area CA. Accordingly, the X-ray generator 13 is moved so as to be close to the CT image area CA from the location LS to the location L01. On this occasion, the revolution reference point CP is moved from the location LSC to the location L01C as shown in FIG. 17B. The X-ray generator 13 is moved so as to be apart from the CT image area CA from the location L13 to the location LEa. On this occasion, the revolution reference point CP is moved from the location L13C to a location LEaC as shown in FIG. 17B.

For example, respective organs of a body (except for specific organs such as a heart and lungs) are positioned so as to be approximately symmetrical in many cases and, for example, a head and the like are approximately symmetrical. In the case where the image object is symmetrical in this manner, it is conceivable that the location of the X-ray absorption portion of a body is approximately symmetrical. Therefore, the right and left portions are subjected to CT imaging in a symmetrical manner under almost same conditions, with the symmetry axis being a boundary, with the result that an angle of incidence of an X-ray, an X-ray amount and the like with respect to the CT image area can be made approximately the same between the right and left areas.

In particular, in CT imaging shown in FIGS. 17A and 17B, the moving trajectory of the X-ray generator 13 is symmetrical with respect to the symmetry axis AQ (approximately coinciding with a symmetry axis of a human body) of the image object OB, and thus the irradiation direction of an X-ray (traveling direction of the optical axis CB of the X-ray cone beam BX1) at respective positions on the moving trajectory also change in a symmetrical manner. This enables to obtain three-dimensional data symmetrical with respect to the symmetry axis AQ in the CT image area CA, and the image quality of the CT image is resistant to variations in the right and left portions thereof. Accordingly, the above-mentioned CT imaging is advantageous in diagnostic imaging.

In CT imaging shown in FIG. 17A, the revolution reference point CP is moved at the locations out of the oval track of the revolution reference point CP, which is drawn between the locations L01C and L13C, while the X-ray generator 13 is moved from the location LS to the location L01 and while the X-ray generator 13 is moved from the location L13 to the location LEa. In any movements, however, the revolution reference point CP may be retained at the location L01C (=location L13C). In this case, while there may be generated non-irradiation areas in the CT image area CA, which are not irradiated with an X-ray, projection data for 180 degrees can be obtained by the remaining imaging also in those areas. Accordingly, there is hardly any problem in generation of a CT image.

The track of the revolution reference point CP in FIG. 17B includes the oval track portion between the location L01C to the location L13C, and the portion between the location L01C and the location L13C and the portion between the location L13C and the location LEaC where the revolution reference point CP moves linearly.

The track of the revolution reference point CP is a line segment extending on the right side from the location L01C being the intersection of an oval longitudinal axis ELL and an oval arc toward the longitudinal axis ELL, that is, extending in the direction perpendicular to the direction in which the X-ray detector 21 becomes close to the CT image area CA, between the location LSC and the location L01C, which is the track traveling from the location LSC being the end of the line segment toward the location L01C.

In addition, the track of the revolution reference point CP is a line segment extending on the left side from the location L01C being the intersection of an oval longitudinal axis ELL and an oval arc toward the longitudinal axis ELL, that is, extending in the direction perpendicular to the direction in which the X-ray detector 21 becomes close to the CT image area CA, between the location L13C and the location LEaC, which is the track traveling from the location L13C being the end of the line segment toward the location LEaC.

Note that the track traveling from the location LSC toward the location L01C and the track traveling from the location L13C toward the location LEaC are not necessarily straight lines, and may be set such that the entire CT image area CA is always fit in the irradiation area of the X-ray cone beam BX1 during CT imaging.

In FIGS. 17A and 17B, there is conceivable another example in which the moving trajectory of the revolution reference point CP draws only an oval shape. For example, the trajectory of the revolution reference point CP may be set so as to move only on an oval track, starting from a location LSCa to a location LECa shown in FIG. 17B. The location LSCa is set at the location L12C shown in FIG. 12 or in the vicinity thereof, while the location LECa is set at the location L02C shown in FIG. 12 or in the vicinity thereof.

While the trajectory of the revolution reference point CP moves linearly between the location LSC and the location L01C and between the location L13C and the location LEaC in the example described above, the track therebetween is changed. That is, at the location LSC, the revolution reference point CP starts from the location LSCa shown in FIG. 17B, moves on the oval track of the revolution reference point CP that is drawn between the location L01C and the location L13C to the location L01C, and moves between the location L01C and the location L13C similarly in the example described above. The revolution reference point CP similarly moves on the oval track to the location LECa after reaching the location L13C. CT imaging in which the revolution reference point CP is moved in this manner may be performed.

1.5. Other CT Imaging 3

Figure 18A:
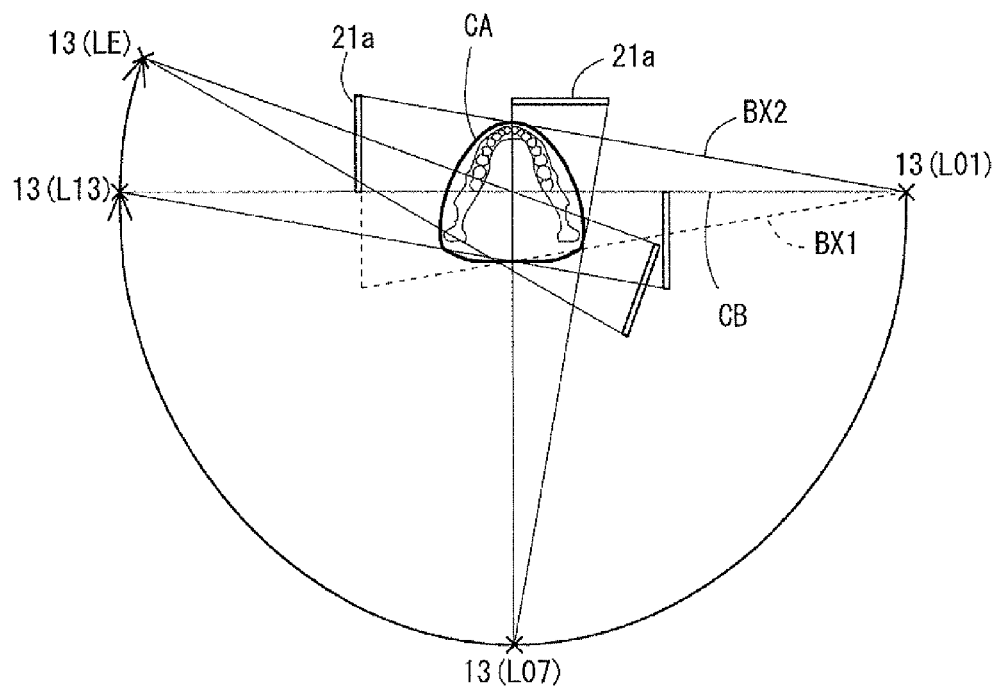
FIGS. 18A and 18B are plan views showing an outline of other CT imaging.
Figure 18B:
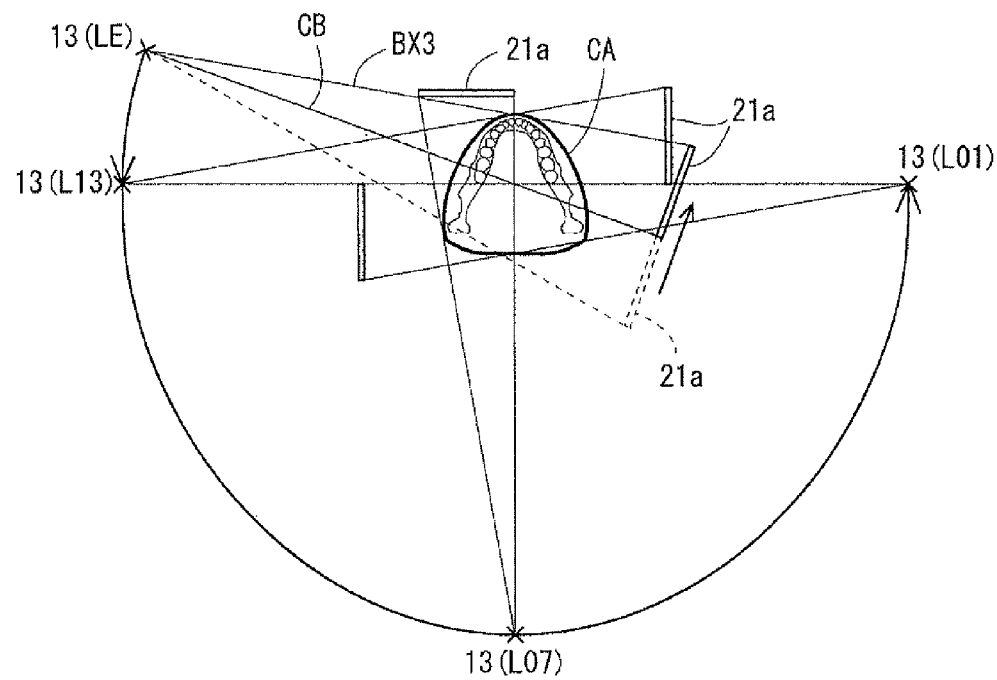

FIGS. 18A and 18B are plan views showing an outline of other CT imaging. FIGS. 18A and 18B show a series of CT imaging by division thereof into the first CT imaging (FIG. 18A) and the latter CT imaging (FIG. 18B). In this CT imaging, as shown in FIG. 18A, the X-ray imaging apparatus 100 first moves the X-ray generator 13 from the location L01 to the location LE similarly in CT imaging shown in FIGS. 14A and 14B. In this case, an X-ray cone beam BX2 emitted from the X-ray generator 13 has the shape obtained by restricting the left half of the X-ray cone beam BX1 along the optical axis CB. That is, the X-ray cone beam BX2 is the right half of the original X-ray cone beam BX1, and the optical axis CB is located on the left outer edge of the X-ray cone beam BX2. The X-ray imaging apparatus 100 detects the X-ray cone beam BX2 with an X-ray detector 21a.

Next, as shown in FIG. 18B, the X-ray imaging apparatus 100 moves the X-ray generator 13 in a reverse manner from the location LE to the location L01 on the same moving path to that of the first CT imaging. An X-ray cone beam BX3 emitted on this occasion has a shape obtained by restricting the right half of the X-ray cone beam BX1 shown in FIG. 14A along the optical axis CB. That is, the X-ray cone beam BX3 is the left half of the X-ray cone beam BX1, and the optical axis CB is located on the right outer edge of the X-ray cone beam BX3. The X-ray imaging apparatus 100 detects the X-ray cone beam BX3 with the X-ray detector 21a moved in a parallel manner toward the left side (in FIG. 18B, the direction indicated by an arrow).

Also in this CT imaging, the projection data of the CT image area CA having an approximately triangular shape can be collected by revolution in which a rotation angle is 180 degrees or more and less than 360 degrees as in CT imaging shown in FIG. 14A. In particular, this CT imaging is advantageous in that a manufacturing cost can be reduced because the X-ray detector 21a can be made small in size to approximately half the size of the X-ray detector 21 shown in FIG. 14A.

1.6. Other CT Imaging 4

While the revolution reference point CP is moved such that the moving trajectory MT has an oval shape during CT imaging in CT imaging shown in FIG. 14A, the moving trajectory of the revolution reference point CP is not limited thereto.

Figure 19A:
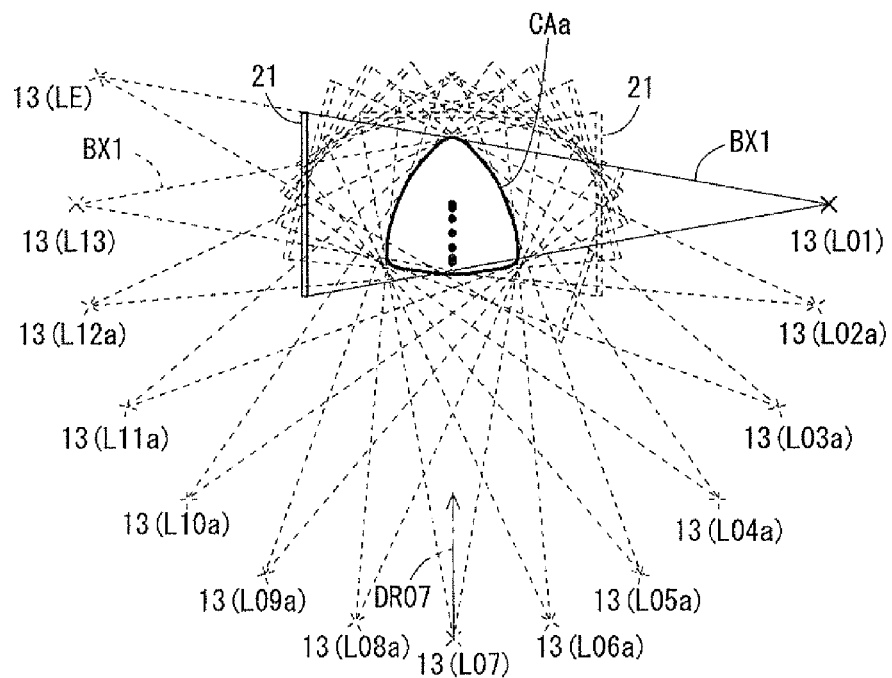
FIGS. 19A and 19B are views for describing an outline of other CT imaging.
Figure 19B:
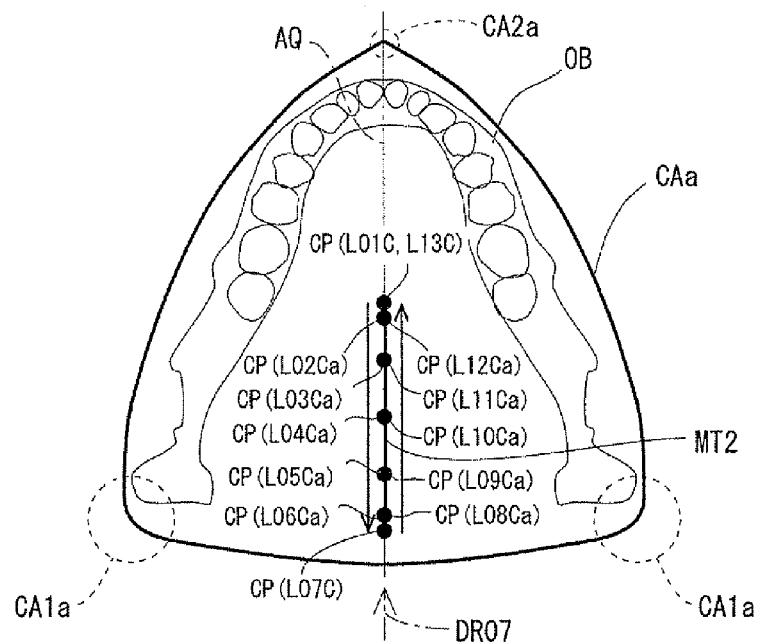

FIGS. 19A and 19B are views for describing an outline of other CT imaging. FIG. 19A shows the outline of CT imaging, while FIG. 19B shows a moving trajectory MT2 of the revolution reference point CP during CT imaging shown in FIG. 19A.

In this CT imaging, as shown in FIG. 19A, the X-ray generator 13 starts X-ray radiation from the location L01, and then the revolution arm 30 is rotated for 180 degrees, whereby the revolution rotation point CP is moved from locations L02a, L03a ... L06a, L07a, L08a ... L12a to L13. On this occasion, as shown in FIG. 19B, the revolution reference point CP is moved so as to move back and forth linearly from the location L01C to the location L07C and return to the location L01C (=location L13C) again. The moving trajectory is a straight line parallel to the symmetry axis AQ of the target image area. The locations L02Ca to L12Ca of the revolution reference point CP correspond to the locations L02a to L12a of the X-ray generator 13, respectively.

Also in the case where the revolution reference point CP is moved in this manner, as shown in FIG. 19B, it is possible to set extending parts CA1a, CA1a extending outwardly on the right and left, and a CT image area CAa having an approximately triangular shape obtained by connecting the extending parts CA1a, CA1a such that the CT image area CAa protrudes upwardly from the extending parts CA1a, CA1a toward a top CA2a. In particular, the CT image area CAa in this CT imaging has a shape that more looks like a Reuleaux triangle being one of shapes of constant width compared with the CT image area CA shown in FIG. 12.

As described above, the CT image area having an approximately triangular shape of this application can be set variously in accordance with the movement control of the revolution reference point. Next, the CT image area is described with reference to FIGS. 22A, 22B, 22C, 22D, 22E, 22F and 22G.

FIGS. 22A, 22B, 22C, 22D, 22E, 22F and 22G are views for describing the examples of the CT image area having an approximately triangular shape, which are ones according to embodiments of the present application.

Figure 22A:
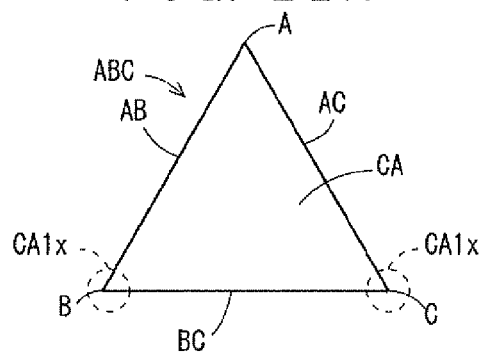
FIGS. 22A, 22B, 22C, 22D, 22E, 22F and 22G are views for describing examples of CT image areas having an approximately triangular shape.

FIG. 22A shows the CT image area CA having a shape of a triangle ABC formed by vertices A, B and C and sides AB, AC and BC. For more detailed description of the embodiment of FIG. 22A, FIG. 22F is now referenced to. The CT image area CA according to the embodiment of FIG. 22A is the area that has the shape of a triangle ABC formed by vertices A, B and C and sides AB, AC and BC. In the example shown in FIG. 22A, the side BC is a base, and the vertex A formed by the connection of the sides AB and AC is opposed to the base BC. The triangle ABC is desirably an isosceles triangle. Needless to say, the triangle ABC may be an equilateral triangle. Similarly to the extending parts CA1, CA1 of FIG. 12, there are extending parts CA1x, CA1x in the vicinity of the vertex B and the vertex C.

Figure 22B:
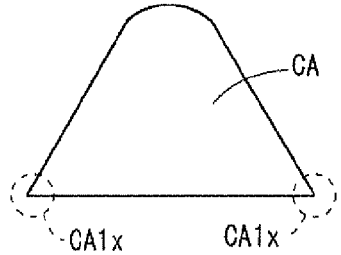

FIG. 22B shows the shape of the CT image area CA according to another embodiment. The CT image area CA according to the present embodiment is partially different from the CT image area CA of FIG. 22A in shape in that the portion of the vertex A of the triangle ABC of FIG. 22A is rounded. That is, the side AB and the side AC are not connected at the vertex A but are connected with a convex curved line in the CT image area CA shown in FIG. 22B.

The line connecting the side AB and the side AC is not necessarily limited to a curved line but may be a straight line (the CT image area CA has a trapezoidal shape) or a partially straight line. In this case, a straight line may include one or a plurality of straight lines.

Now, FIG. 22F is referenced to for more detailed description of the embodiment of FIG. 22B. The CT image area CA according to the embodiment of FIG. 22B is the area that has a shape surrounded by the base BC, a line ABb, a line AB1, a line AR, a line AC1 and a line ACb. The side AB is formed by a line ABa of the area close to the vertex A, the line ABb of the area close to the vertex B and the line AB1 of the area far apart from the vertices A and B. The side AC is formed by a line ACa of the area close to the vertex A, the line ACb of the area close to the vertex C and the line AC1 of the area apart from the vertices A and C. The line AB1 and the line AC1 are connected with the line AR that is desirably located on an inner side of the triangle ABC compared with the vertex A. In the example shown in FIG. 22B, the line AB1 and the line AC1 are connected with the arc AR. The arc AR has a convex side and a concave side, and the arc AR has a convex side directed outwardly toward the outside of the triangle ABC. That is, the arc AR is convexed.

Figure 22C:
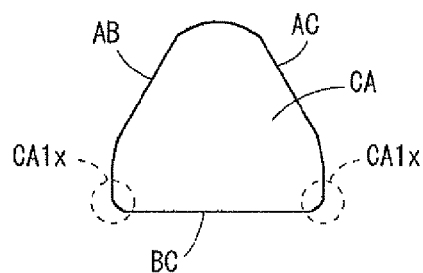

FIG. 22C shows the shape of the CT image area CA according to another embodiment. The CT image area CA of the present embodiment is partially different from the CT image area CA of FIG. 22B in shape in that the portions of the vertices B and C of the triangle ABC of FIG. 22A, that is, the right and left portions of the side BC being the base are rounded. That is, the side AB and the side BC are not connected at the vertex B but are connected with a convex curved line. The side AC and the side BC are not connected at the vertex C but are connected with a convex curved line, with the straight portions AB1 and AC1 being left.

The line connecting the side AB and the side BC and the line connecting the side AC and the side BC are not necessarily limited to curved lines but may be straight lines or partially straight lines. In this case, the straight line may include one or a plurality of straight lines.

Now, FIG. 22F is referenced to for more detailed description of the embodiment of FIG. 22C. The CT image area CA according to the embodiment of FIG. 22C is an area having a shape surrounded by a line BC1, a line BR, the line AB1, the line AR, the line AC1 and a line CR. The side BC is formed by a line BCa of the area close to the vertex B, a line BCb of the area close to the vertex C and the line BC1 of the area apart from the vertices B and C. The side AC is formed of the line ACa of the area close to the vertex A, the line ACb of the area close to the vertex C and the line AC1 of the area apart from the vertices A and C. The lines AB and AC are identical to those of the example shown in FIG. 22B, and thus detailed description thereof is omitted.

The line AB1 and the line BC1 are connected with a line BR that is desirably located on an inner side of the triangle ABC compared with the vertex B. The line AC1 and the line BC1 are connected with a line CR that is desirably located on an inner side of the triangle ABC compared with the vertex C. In the example shown in FIG. 22C, the line AB1 and the line BC1 are connected with the arc BR, while the line AC1 and the line BC1 are connected with the arc CR. The arcs BR and CR have a convex side and a concave side, and in this case, the arcs BR and CR have a convex side directed toward the outside of the triangle ABC. That is, the arcs BR and CR are convexed.

Figure 22D:
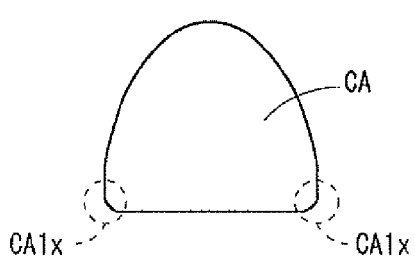

FIG. 22D shows the shape of the CT image area CA of another embodiment. The CT image area CA of the present embodiment is different from the CT image area CA of FIG. 22C in shape in that the straight line portions AB1 and AC1 are deformed to convex curved line portions.

The lines deformed from the sides AB and AC are not necessarily limited to curved lines and may be partially straight lines. In this case, the straight line may include one or a plurality of straight lines.

Now, FIG. 22F is referenced to for more detailed description of the embodiment of FIG. 22D. The CT image area CA according to the embodiment shown in FIG. 22D is the area having the shape surrounded by the line BC1, the line BR, a line ABR, a line ACR and the line CR. The example of FIG. 22D is identical to that of FIG. 22C except for that the lines AB1 and AC1 are replaced with the lines ABR and ACR, and thus detailed description thereof is omitted.

The lines AB1 and AC1 of the example shown in FIG. 22C are replaced with the lines ABR and ACR passing outside the triangle ABC. In the example shown in FIG. 22D, the lines ABR and ACR are arcs ABR and ACR. The arcs ABR and ACR have a convex side and a concave side, and in this case, the arcs ABR and ACR have a convex side directed outside the triangle ABC. That is, the arcs ABR and ACR at the center portion of the side AB and the side BC are convexed. The arcs ABR and ACR may be deformed to be convexed lines including a plurality of straight lines.

The arc BR, the arc ABR, the arc AR, the arc ACR and the are CR may be set to have the same or almost the same curvature so as to form an approximately semi-circle such as a semi circle, as long as the image object OB is fit therein efficiently. The approximately semi-circle in this case is not limited to a completely round semi-circle and may be one having partially different curvatures in an arc or one having a horseshoe shape.

Preferably, the arc BR, the arc ABR, the arc AR, the arc ACR and the arc CR are connected smoothly without generating any inflection point. In this case, the CT image area CA has an approximately semi-circular shape as shown in FIG. 22G.

Figure 22E:
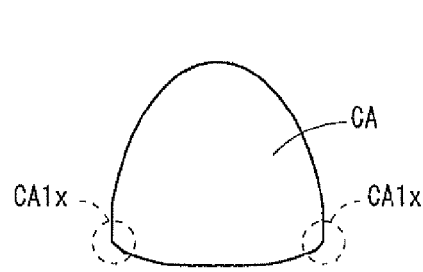
Figure 22F:
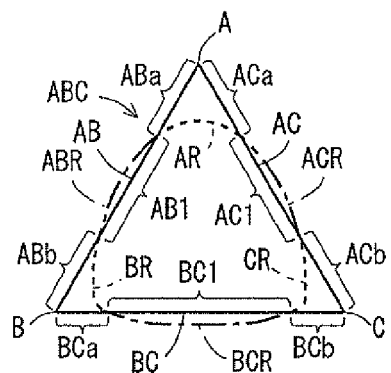
Figure 22G:
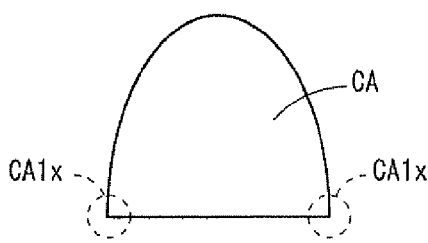

FIG. 22E shows the shape of the CT image area CA of another embodiment. The CT image area CA of the present embodiment has the shape partially different from that of the CT image area CA of FIG. 22D in shape in that the side BC is deformed to be a convexed curved line. The line obtained by deforming the side BC is not necessarily limited to a curved line and partially may be a straight line. In this case, a straight line may include one or a plurality of straight lines.

Now, FIG. 22F is referenced to for more detailed description of the embodiment shown in FIG. 22E. The CT image area CA according to the embodiment shown in FIG. 22D is the area having the shape surrounded by a line BCR, the line BR, the line ABR, the line AR, the line ACR and the line CR. The example of FIG. 22E is identical to that of FIG. 22 except for that the line BC1 is replaced with the line BCR, and thus detailed description thereof is omitted.

In the example of FIG. 22E, the line BC1 of the example of FIG. 22D is replaced with the line BCR passing outside the triangle ABC, and the line BCR is the base of an approximate triangle. In the example shown in FIG. 22E, the line BCR is an arc BCR. The arc BCR has a convex side and a concave side and, in this case, the arc BCR has a convex side directed outside the triangle ABC. That is, the arc BCR is convexed. The arc BCR may be deformed so as to be convexed lines formed of a plurality of straight lines.

The arc BR, the arc ABR, the arc AR, the arc ACR and the arc CR may be set to have the same or almost the same curvature so as to form an approximately semi-circle such as a semi circle, as long as the image object OB is fit therein efficiently. The approximate semi-circle in this case is not limited to a completely round semi-circle and may be one having partially different curvatures in an arc or one having a horseshoe shape.

Preferably, the arc BR, the arc ABR, the arc AR, the arc ACR and the arc CR are connected smoothly without generating any inflection point. In this case, the CT image area CA has an approximately semi-circular shape (more strictly, shape of the moon on the thirteenth night).

As described above, the CT image area CA has the extending parts CA1x, CA1x in any of FIGS. 22A, 22B, 22C, 22D, 22E, 22F and 22G, similarly to the extending parts CA1, CA1 of FIG. 12. In FIGS. 22D and 22E, the CT image area CA has the extending parts CA1x, CA1x on its lower side, that is, on the right and left of the side BC or the line BCR that is the base, and an approximately triangular shape is symmetrical in which the extending parts CA1x, CA1x on the right and left and the top are connected with the curved lines ABR and ACR from the right and left extending parts CA1x, CA1x toward the portion in the vicinity of the top A that is the top.

It suffices that the image object OB is appropriately fit in the CT image area CA with economy, and the CT image area CA may be somewhat deformed in a range so as not to cause any problem for that object. For example, the curvatures of the arcs AR, BR, CR, ABR, ACR and BCR can be set in a various manner. The curvatures of the arcs AR, BR and CR may be set to be smaller than the curvatures of the arcs ABR, ACR and BCR.

1.7. Other CT Imaging

While the entire jaw including teeth is set as the image object OB in the CT image area CA in CT imaging shown in FIGS. 14A, 14B and the like, the image object may include only teeth.

Figure 20:
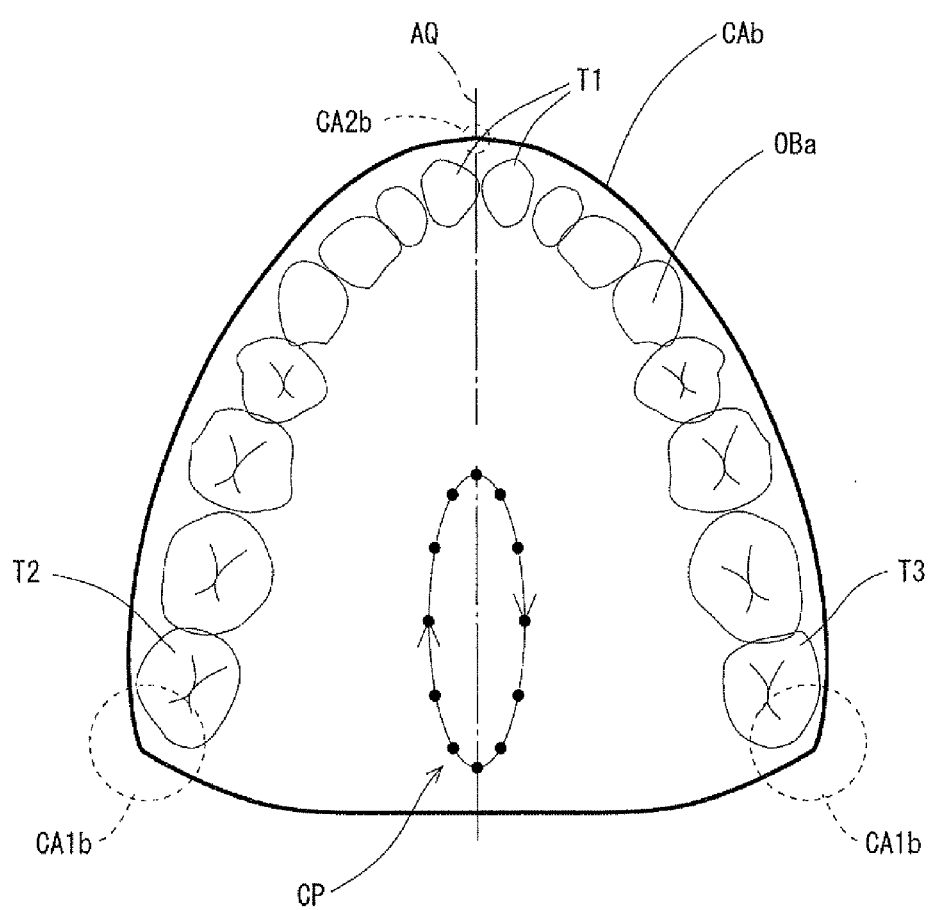
FIG. 20 shows the state in which a CT image area is set so as to include only teeth.

FIG. 20 shows the state in which a CT image area CAb is set so as to include only teeth. In this CT imaging, a dental arch model (imaginary image object OBa), which is obtained from the data of a standard dental arch shape set from a standard arrangement of teeth), is prepared in advance. The above-mentioned dental arch model is stored in, for example, the storage part 802. When an operator sets the image area, the CT image area CAb is set such that the front teeth T1 of the dental arch model are arranged inside the boundary on the front side of the CT image area CAb (in the vicinity of a top CA2b) and that the left molar T2 and the right molar T3 of the dental arch model are arranged inside the boundary on the left rear side and the right rear side of the CT image area CAb (in the vicinity of extending parts CA1b, CA1b), respectively. The front teeth T1, the molars T2 and T3 of the dental arch model OBa are entirely fit in the CT image area CAb in this manner.

The CT image area CAb having an approximately triangular shape is set in this manner, with the result that CT imaging of the entire teeth can be easily performed. In particular, typical teeth form a dental arch (that is, have an arch shape), and thus it is effective to set the CT image area CAb having an approximately triangular shape in CT imaging. Through control similarly to that of CT imaging shown in FIG. 14A, it is possible to perform CT imaging of the CT image area CAb set as described above.

2. Second Embodiment

FIGS. 21A and 21B schematically show the outline of an X-ray imaging apparatus 100A according to a second embodiment. FIG. 21A is a front view of the X-ray imaging apparatus 100A, and FIG. 21B is a side view of the X-ray imaging apparatus 100A. In the following description, components having similar functions to those of the first embodiment are denoted by the same symbols, and description thereof is omitted.

As shown in FIG. 21A, the X-ray imaging apparatus 100A according to the present embodiment has the structure in which the revolution arm 30 is suspended at the center location of an upper frame 41A that is supported on both side ends by two support columns 50A. Therefore, the present embodiment is free from a fear that the revolution arm 30 may interfere with a mechanical component such as the support column 50 according to the first embodiment, and the revolution arm 30 is configured so as to revolve in the range of 360 degrees.

The both side ends of the upper frame 41A are connected to belts 51 looped across pulleys inside the support columns 50A. When the belts 51 are turned by driving of a motor (not shown), the upper frame 41A is caused to move up and down along the vertical direction.

The X-ray imaging apparatus 100A includes a headrest or the like for fixing a human head being the object M1, and is provided with an object fixing part 421A configured as a seat. The object fixing part 421A fixes the object M1 in a sitting position. The object fixing part 421A is supported from the bottom side thereof by an elevator part 63 that moves up and down in the vertical direction.

The revolution arm 30 is connected to the XY-table 35 (composed of the X-table 35X and the Y-table 35Y) contained in the upper frame 41A by the revolution shaft 31, and is capable of moving in the horizontal direction with respect to the upper frame 41A. The object fixing part 421A is connected to an XY-table 64 having a function similar to that of the XY-table 35, and is configured so as to move in the horizontal direction with respect to the upper frame 41A.

In the X-ray imaging apparatus 100A configured as described above, the object fixing part 421A configured as a seat is moved in a horizontal plane, whereby the revolution arm 30 being the support part can be moved relative to the object. It is effective to practice the present invention also in the X-ray imaging apparatus configured as described above.

3. Modifications

Although embodiments of the present invention have been described above, the present invention is not limited to the above-described embodiments, and various modifications can be made.

For example, although the pyramid-shaped X-ray beam is radiated to the target image area by causing the X-ray beam to pass through the beam passing hole 151 formed as a rectangular opening in X-ray CT imaging in the above-described embodiments, a cone-shaped X-ray beam may be radiated by forming the beam passing hole 151 into a circular shape.

Further, while the functional block described in the embodiments above is described to be implemented as software, a part or the whole of the functional block may be implemented as hardware by a dedicated logic circuit.

The X-ray CT imaging apparatus 100 according to the above-described embodiment is structured so as to vertically stand on a floor. However, needless to say, the X-ray CT imaging apparatus 100 is applicable to one having a structure in which CT imaging is performed with the subject, that is, the object M1, taking a lying posture. For example, it is possible to set the extending direction of the revolution shaft 31 to be horizontal and change the object fixing part 421 to, for example, a bed or the like on which a patient is placed horizontally.

Further, an approximately triangular shaped CT image area is set in the present invention, and hence the present invention is preferable in a case where an image object is jaw, teeth and the like having an approximately triangular shape. Needless to say, however, an image object may be other organ. Moreover, the present invention is applicable in a case where an object is other animal.

Further, while the above-mentioned embodiments have described the movement mechanism for driving the XY-table 35 as shown in FIG. 9, the movement mechanism is not limited thereto.

FIGS. 23A and 23B are views for describing a movement mechanism according to the modification. FIG. 23A schematically shows the movement mechanism. The movement mechanism of FIGS. 23A and 23B are controlled based on the polar coordinates, and a revolution arm is moved by driving of two arms AM1 and AM2. FIG. 23B shows the state in which the X-ray generator 13, the positions of the revolution shaft 31 (indicated by (+) in FIGS. 23A and 23B) and the position of the X-ray detector 21 correspond to three phases in which the revolution arm is revolved at 90-degree increments in revolution angle.

A rotation reference point PT1 is fixed with respect to a main body 1 (not shown), and one end of the first arm AM1 is turnably supported with the rotation reference point PT1 being the fulcrum. Moreover, one end of the arm AM2 is turnably supported by the other end of the arm AM1, and the revolution shaft 31 of the revolution arm, whose position is indicated by (+) in FIGS. 23A and 23B, is turnably supported by the other end of the second arm AM2. The revolution arm is driven to revolve about the axis of the revolution shaft 31 by a driving motor (not shown) or the like. The revolution shaft 31 may be fixed to the other end of the second arm AM2 so as not to rotate so that the revolution arm is revolved about the revolution shaft 31.

The revolution shaft 31 is the revolution reference point CP in the example shown in FIGS. 23A and 23B. FIG. 23A does not show the revolution arm and the X-ray cone beam but shows only the optical axis CB. The arms AM1 and AM2 are controlled by a driving motor (not shown), which is coupled to each thereof so as to control a rotation angle and serves for arm driving, to be rotated. A rotation angle θ2 of the arm AM1 with respect to the main body 1 of the X-ray imaging apparatus and a relative rotation angle θ3 of the arm AM2 with respect to the arm AM1 are controlled, whereby it is possible to control the position (+) of the revolution shaft 31 in a two-dimensional plane perpendicular to the revolution shaft 31. The movement mechanism shown in FIGS. 23A and 23B moves the revolution arm (that is, support part) relative to the object M1 in a two-dimensional plane perpendicular to the revolution shaft 31. The movement mechanism according to the modification has been described above.

The X-ray imaging apparatus of the present application may be configured so as to perform not only X-ray CT imaging of a CT image area having an approximately triangular shape but also X-ray CT imaging of X-ray CT imaging of a CT image area having other shape. For example, it is possible to perform X-ray CT imaging of a circular CT image area, which has been conventionally known, in addition to X-ray CT imaging of a CT image area having an approximately triangular shape. This is described with reference to FIG. 12.

FIG. 12 shows the CT image area CA having an approximately triangular shape. As described above, it is possible to perform X-ray CT imaging in which a jaw being an image object OB is fit in the CT image area CA having an approximately triangular shape. While, FIG. 12 shows the CT image area CAc having a circular shape with the intersection IS being the center of a circle. The X-ray imaging apparatus may be configured so as to perform X-ray CT imaging of the CT image area CAc having a circular shape in addition to X-ray CT imaging of the CT image area CA having an approximately triangular shape.

X-ray CT imaging of the CT image area CAc is performed when the X-ray generator 13 and the X-ray detector 21 set the fixed revolution center thereof to the intersection IS and then are revolved thereabout. The CT image area CAc has almost the same size as that of the CT image area CA having an approximately triangular shape. In the case of X-ray CT imaging for the CT image area CAc, partial areas of both jaw joints are out of the CT image area by an amount for performing X-ray CT imaging without moving the revolution reference point, but the entire teeth area is included in the CT image area. Therefore, a CT image including the entire teeth can be obtained in X-ray CT imaging of the CT image area CAc.

X-ray CT imaging of the CT image area CAc is advantageous in that mechanical accuracy is easily enhanced thanks to simple revolution in the case where, as shown in FIG. 12, X-ray CT imaging is performed when the X-ray generator 13 and the X-ray detector 21 set the fixed revolution center thereof to the intersection IS and then are revolved thereabout.

As described above, according to this modification, it is possible to select any of the CT imaging mode for a CT image area having an approximately triangular shape and the CT imaging mode in which the revolution center is fixed in imaging.

Further, selection may be made between the CT imaging mode for a CT image area having an approximately triangular shape in which the entire jaw area is included in the CT image area and the CT imaging mode in which the revolution center of the X-ray generator 13 and the X-ray detector 21 in imaging is fixed without moving the revolution reference point in the CT imaging mode for a CT image area having an approximately triangular shape.

As can be seen from the cross section of the CT image area in the horizontal direction, it is possible to select any of the CT imaging mode for a CT image area having an approximately triangular shape and the CT imaging mode for a CT image area having a circular shape. In the case where the circular CT image area is a completely round CT image area, the CT imaging mode for a CT image area having a circular shape is the CT imaging mode for a CT image area having a completely round shape.

Accordingly, in a case where, for example, X-ray CT imaging is performed for the entire jaw including right and left jaw joints, the CT imaging mode for a CT image area having an approximately triangular shape is performed. While, in a case where a CT image is only required to include all teeth bus is not required to include the entire right and left jaw joints, the CT imaging mode in which the revolution center is fixed in imaging is performed. In this manner, the X-ray imaging apparatus can be used in accordance with a purpose. The revolution center of the X-ray generator 13 and the X-ray detector 21 can be set to a desired place with the above-mentioned movement mechanism. This allows X-ray CT imaging in which the fixed revolution center in imaging of the X-ray generator 13 and the X-ray detector 21 is positioned at a location closer to the front teeth than the intersection IS.

X-ray CT imaging may be performed for only an area of a partial jaw, in which the CT image area is narrower than the CT image area having an approximately triangular shape, in addition to a CT image area having an approximately triangular shape. X-ray CT imaging performed for only a partial area of a jaw, which has a smaller CT image area than the CT image area having an approximately triangular shape, is referred to as jaw local CT imaging.

Conceivable examples of the target area of the jaw local CT imaging in a case where the CT image area having an approximately triangular shape has the entire jaw include the area including only the entire teeth of the jaw, the area of the teeth including only a part of the entire teeth, the area including only any of the right and left jaw joints, and the area including any of the right and left jaw joints and a part of the teeth continuous from the jaw joint. This is described with reference to FIG. 24.

Figure 24:
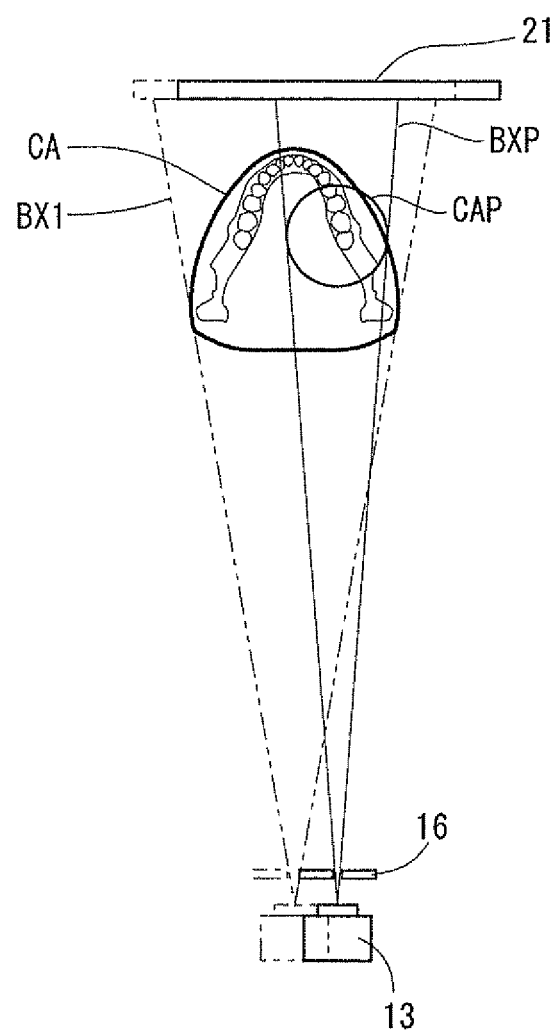
FIG. 24 is a view for describing X-ray CT imaging according to another modification

FIG. 24 is a view for describing X-ray CT imaging according to a modification. In FIG. 24, an area of a part of the right teeth among the entire teeth is a CT image area (jaw local area) CAP.

An X-ray beam is restricted such that only the CT image area CAP is always irradiated with an X-ray during X-ray CT imaging, and is radiated as an X-ray cone beam BXP. The above-mentioned horizontal beam shaping mechanism adjusts the spread of the X-ray beam in the horizontal direction. The X-ray generator 13 and the X-ray detector 21 are revolved about the center of the CT image area CAP as the fixed revolution center, whereby X-ray CT imaging is performed. The above-mentioned X-ray CT imaging mode is referred to as the CT imaging mode for a jaw local area.

Through the selection of a CT imaging mode for a local area of a jaw, X-ray CT imaging in which an X-ray is radiated only to a minimum required area can be performed in a case where only a CT image of a partial area of a jaw is required. The revolution center of the X-ray detector 13 and the X-ray detector 21 can be set to a desired location with the above-mentioned movement mechanism. In FIG. 24, the X-ray generator 13 and the X-ray detector 21 are revolved about the CT image area CAP serving as the fixed revolution center and perform X-ray CT imaging.

As described above, according to this modification, it is possible to select any of the CT imaging mode for a CT image area having an approximately triangular shape and the CT imaging mode for a local area of a jaw. Note that in the above-mentioned configuration in which any of the CT imaging mode for a CT image area having an approximately triangular shape and the CT imaging mode in which the revolution center is fixed in imaging, the X-ray imaging apparatus may be configured so as to further select a CT imaging mode for a local area of a jaw.

As another modification, the X-ray imaging apparatus may be configured so as to change the size of the CT image area having an approximately triangular shape. Specifically, the X-ray imaging apparatus may be configured so as to selectively perform X-ray CT imaging for the CT image area CAb including only the teeth shown in FIG. 20 or X-ray CT imaging for the CT image area CA including the entire jaw shown in FIG. 12. In this case, the above-mentioned horizontal beam shaping mechanism can adjust the spread of the X-ray beam in the horizontal direction. Further, the above-mentioned movement mechanism can set the revolving trajectory of the X-ray generator 13 and the X-ray detector 21.

The configurations of the respective embodiments and modifications described above may be appropriately combined, unless they are not contradictory with each other.

What is claimed is:

1. An X-ray CT imaging method for performing X-ray CT imaging comprising:
    a supporting step of supporting an X-ray generator that generates an X-ray cone beam, and an X-ray detector that detects the X-ray cone beam radiated to a subject by a support part with the subject located therebetween;
    a revolving step of revolving the support part relative to the subject by a revolution driving part in the supporting step;
    a moving step of moving the support part relative to the subject on a two-dimensional plane orthogonal to a revolution shaft of the revolution driving part by movement mechanisms in the revolving step; and
    a controlling step of controlling the revolution driving part and the movement mechanisms in an interlocking manner such that a CT image area has an approximately triangular shape, the CT image area being imaged by irradiation of the X-ray cone beam by revolving the support part in the revolving step.

2. The X-ray CT imaging method according to claim 1 and further comprising, in the controlling step, controlling the revolution driving part and the movement mechanisms, in revolving movements of the X-ray generator and the X-ray detector with the subject being located therebetween, in an interlocking manner such that a distance between the X-ray detector and any one of right and left ends of a target image area that is closer to the X-ray detector when the X-ray detector is located on any one of the right and left ends of the target image area is larger than a distance between the X-ray detector and a top of the target image area when the X-ray detector is located on a symmetry axis passing through the top of the target image area opposed to a base thereof.

3. The X-ray CT imaging method according to claim 1 and further comprising, in the controlling step, forming the approximately triangular shape by rounding a top portion of an isosceles triangle opposed to a base thereof into a convex arc.

4. The X-ray CT imaging method according to claim 1 and further comprising, in the controlling step, forming the approximately triangular shape by rounding portions at both ends of a base of an isosceles triangle into a convex arc.

5. The X-ray CT imaging method according to claim 1 and further comprising, in the controlling step, forming the approximately triangular shape by forming center portions of at least two sides other than a base of an isosceles triangle into a convex arc.

6. The X-ray CT imaging method according to claim 1 and further comprising, in the controlling step, forming the approximately triangular shape in a symmetrical shape by connecting extending parts on right and left sides of a base of the triangular shape and a top of the triangular shape by a curved line.

7. The X-ray CT imaging method according to claim 2 and further comprising, in the controlling step, controlling the revolution driving part and the movement mechanisms, during X-ray CT imaging, in an interlocking manner such that a revolution reference point set on an optical axis of the X-ray cone beam generates an oval-shaped moving trajectory while revolving the support part relative to the subject for an amount of a rotation angle of 180 degrees or more and less than 360 degrees.

8. The X-ray CT imaging method according to claim 7 and further comprising, in the controlling step:
- revolving the support part by the revolution driving part about the revolution shaft relative to the subject secured at a predetermined position; and
- using the revolution shaft as the revolution reference point of the X-ray cone beam.

9. The X-ray CT imaging method according to claim 1 and further comprising, in the controlling step, controlling the revolution driving part, during CT imaging, so as to revolve the support part in a relative manner for an amount of a rotation angle obtained by adding an angle of broadening of the X-ray cone beam to 180 degrees in a revolution direction.

10. The X-ray CT imaging method according to claim 1 and further comprising, a setting step for setting the CT image area such that front teeth and right and left molars of a dental arch model are entirely fit therein, the dental arch model being data obtained from a standard arrangement of teeth and having a standard dental arch shape.

11. The X-ray CT imaging method according to claim 1 and further comprising, an X-ray irradiation controlling step of temporarily increasing, during the X-ray CT imaging, an X-ray amount radiated to the subject in an irradiation state in which the X-ray cone beam radiated to the subject passes through a cervical spine of a head as the subject and then passes through a jaw thereof.

12. The X-ray CT imaging method according to claim 1 and further comprising, a selecting step of selecting between X-ray CT imaging in which the CT image area has an approximately triangular shape and X-ray CT imaging in which a CT image area has a circular shape upon the X-ray generator and the X-ray detector being revolved about a fixed revolution center in imaging.

13. The X-ray CT imaging method according to claim 1 and further comprising, a selecting step of selecting between X-ray CT imaging in which the CT image area has an approximately triangular shape and X-ray CT imaging for a jaw local area in which X-ray CT imaging is performed only for a partial area of a jaw smaller than the CT image area having an approximately triangular shape upon the X-ray generator and the X-ray detector being revolved about the partial area of the jaw serving as a fixed revolution center in imaging.

* * * * *